US011041005B2

(12) United States Patent
Dalmau

(10) Patent No.: US 11,041,005 B2
(45) Date of Patent: Jun. 22, 2021

(54) METHODS FOR DETECTING AUTOANTIBODIES AGAINST A GABA(A) RECEPTOR ALPHA 1 SUBUNIT AND/OR BETA 3 SUBUNIT IN AUTOIMMUNE SEIZURE AND/OR ENCEPHALITIS

(71) Applicants: INSTITUT D'INVESTIGACIONES BIOMÈDIQUES AUGUST PI I SUNYER, Barcelona (ES); INSTITUCIÓ CATALANA DE RECERCA I ESTUDIS AVANCATS, Barcelona (ES)

(72) Inventor: Josep Dalmau, Barcelona (ES)

(73) Assignees: INSTITUT D'INVESTIGACIONES BIOMEDIQUES AUGUST PI I SUNYER, Barcelona (ES); INSTITUCIO CATALANA DE RECERCA I ESTUDIS AVANCATS, Barcelona (ES)

( * ) Notice: Subject to any disclaimer, the term of this patent is extended or adjusted under 35 U.S.C. 154(b) by 40 days.

(21) Appl. No.: 15/023,131

(22) PCT Filed: Oct. 16, 2014

(86) PCT No.: PCT/EP2014/072252
§ 371 (c)(1),
(2) Date: Mar. 18, 2016

(87) PCT Pub. No.: WO2015/055776
PCT Pub. Date: Apr. 23, 2015

(65) Prior Publication Data
US 2016/0326227 A1 Nov. 10, 2016

(30) Foreign Application Priority Data

Oct. 17, 2013 (EP) ..................................... 13189172

(51) Int. Cl.
A61K 38/00 (2006.01)
G01N 33/564 (2006.01)
C07K 14/47 (2006.01)
G01N 33/94 (2006.01)

(52) U.S. Cl.
CPC ....... C07K 14/4713 (2013.01); G01N 33/564 (2013.01); G01N 33/9426 (2013.01); A61K 38/00 (2013.01); G01N 2333/70571 (2013.01); G01N 2800/2857 (2013.01)

(58) Field of Classification Search
CPC .. A61K 38/00; A61K 2039/505; A61K 48/00; C07K 16/00; C07K 16/2866; C07K 14/4713; C07K 16/18; C07K 2317/14; C07K 14/47; C07K 16/4241; C07K 2317/21; C07K 2317/76; G01N 33/6896; G01N 2333/47; G01N 2800/28; G01N 2333/70571; G01N 2800/2857; G01N 2800/7095; G01N 33/6854; G01N 33/9426
See application file for complete search history.

(56) References Cited

U.S. PATENT DOCUMENTS

| | | | | |
|---|---|---|---|---|
| 5,529,898 A | * | 6/1996 | Rogers | C07K 16/4258 435/7.1 |
| 6,010,854 A | * | 1/2000 | Rogers | C07K 14/70571 435/6.16 |
| 7,029,870 B1 | | 4/2006 | Hanna et al. | |
| 7,601,335 B2 | * | 10/2009 | McCutcheon | G01N 33/564 424/9.2 |
| 7,820,398 B2 | * | 10/2010 | Dambinova | G01N 33/564 435/7.21 |
| 8,728,730 B2 | * | 5/2014 | Dennis, Jr. | A61K 38/16 435/6.11 |
| 9,128,101 B2 | * | 9/2015 | Halbert | C12Q 1/6883 |
| 2004/0219545 A1 | * | 11/2004 | Rando | B82Y 30/00 435/6.12 |
| 2009/0029388 A1 | * | 1/2009 | Beeson | G01N 33/564 435/7.1 |
| 2011/0052488 A1 | * | 3/2011 | Dennis, Jr. | A61K 38/16 424/1.49 |

(Continued)

FOREIGN PATENT DOCUMENTS

FR 2986331 * 2/2013 .......... G01N 33/543
KR 10 2009 0099339 9/2009

(Continued)

OTHER PUBLICATIONS

Pawson et al. 2003, Science 300:445-452.*
Burgess et al. J of Cell Bio. 1990, 111:2129-2138.*
Bowie et al. Science, 1990, 247:1306-1310.*
Lancaster et al. Lancet Neurol. 2010; 9: 67-76.*
Quek et al. Arch Neurol. 2012; 69:582-593.*
Ohkawa et al., J. Neurosci. 2014; 34:8151-8163.*
Nutt. J. Clin. Sleep Med. 2006; 2:S7-S11.*
Fritschy, J-M et al. "GABA-A-Receptor Heterogeneity in the Adult Rat Brain: Differential Regional and Cellular Distribution of Seven Major Subunits", Journal of Comparative Neurology, vol. 359, No. 1, XP002721748; ISSN: 0021-9967; pp. 154-194 (1995).

(Continued)

Primary Examiner — Chang-Yu Wang
(74) Attorney, Agent, or Firm — Grüneberg and Myers PLLC

(57) ABSTRACT

The present invention provides a use of a GABA(A)R, GABA(A)R fragment, or homolog thereof or a cell expressing the GABA(A)R, GABA(A)R fragment, or homolog thereof for the prognosis, diagnosis or treatment of an autoimmune disease in a subject, methods of prognosticating, diagnosing or treating an autoimmune disease, an autoantibody binding to a GABA(A)R, GABA(A)R fragment, or homolog thereof, a method for isolating an antibody binding to a GABA(A)R, GABA(A)R fragment, or homolog thereof, and a test kit, pharmaceutical composition and medical or diagnostic device comprising a GABA(A)R, GABA(A)R fragment, or homolog thereof.

10 Claims, 9 Drawing Sheets
Specification includes a Sequence Listing.

(56) References Cited

U.S. PATENT DOCUMENTS

| | | | | |
|---|---|---|---|---|
| 2011/0236903 | A1* | 9/2011 | McClelland | C12Q 1/6886 435/6.14 |
| 2014/0011861 | A1* | 1/2014 | McClelland | C12Q 1/6886 514/44 A |
| 2014/0341887 | A1* | 11/2014 | Dennis, Jr. | A61K 38/16 424/133.1 |
| 2014/0363422 | A1* | 12/2014 | Hayday | C07K 16/065 424/131.1 |
| 2015/0018251 | A1* | 1/2015 | Lesage | G01N 33/6845 506/18 |
| 2015/0355177 | A1* | 12/2015 | Komorowski | C12N 9/14 435/7.92 |
| 2016/0311876 | A1* | 10/2016 | Miske | C07K 14/4713 |
| 2017/0153234 | A1* | 6/2017 | Vincent | G01N 33/564 |

FOREIGN PATENT DOCUMENTS

| | | | | |
|---|---|---|---|---|
| WO | WO02/29418 | A1 | 4/2002 | |
| WO | 2007/068982 | | 6/2007 | |
| WO | WO2009/114740 | A2 | 9/2009 | |
| WO | 2011/041433 | | 4/2011 | |
| WO | 2013/113864 | A1 | 8/2013 | |
| WO | WO2013/113864 | * | 8/2013 | ........... G01N 33/543 |
| WO | WO2015/177512 | * | 11/2015 | ........... G01N 33/564 |

OTHER PUBLICATIONS

PCT, International Search Report and Written Opinion, PCT/EP2014/072252 dated Apr. 23, 2015, 9 pages.

Schofied, P.R. et al. Sequence and expression of human GABAA receptor alpha1 and beta1 subunits; FEBS Letters, Elsevier, Amsterdam, NL, vol. 244, No. 2; XP025603662; ISSN: 0014-5793; pp. 361-364 (Feb. 27, 1989).

Connor, J. X. et al. GABA-A alpha-1-EGFP fusion protein requires a beta subnit for functional surface expression (Abstract); Society for Neuroscience Abstracts; vol. 23, No. 1-2; XP002721700; 27th Annual Meeting of the Society for Neuroscience, Part 1; New Orleans LA ; ISSN: 0190-5295; p. 112 (Oct. 25-30, 1997).

Petit-Pedrol, M. et al. Encephalitis with refractory seizures, status epilepticus, and antibodies to the GABAA receptor: a case series, characterization of the antigen, and analysis of the effects of antibodies.; Lancet Neurology; vol. 13, No. 3; XP002721702; ISSN: 1474-4465; pp. 276-286 (Mar. 2014).

Mathieu et al., Defective cerebral gamma-aminobutyric acid-A receptor density in patients with systemic lupus erythematosus and central nervous system involvement. An observational study, paper, Lupus (2010) http://lup.sagepub.com , 10 pages.

European Office Action, Appl No. 14786173.6-1402, dated Jun. 23, 2017, 5 pages.

Office Action dated Jun. 4, 2019 in Chinese Application No. 201480052000.4 with English translation (23 pages).

Office Action dated May 27, 2019 in European Application No. 14 786 173.6 (79 pages).

Office Action dated Nov. 28, 2019 in Chinese Application No. 201480052000.4 with English translation.

Chuang et al., The Journal of Pharmacology and Experimental Therapeutics, Feb. 2018, 364:180-197.

Ding et al., the Journal of Biological Chemistry, 2010; 285(34): 26390-26405.

Tanaka et al., The American Journal of Human Genetics; 2008; 82:1249-1261.

$GABA_A$ receptor, Wikipedia, retrieved Mar. 17, 2020 from URL:/en.wikipedia.org/wiki/GABAA_receptor, 13 pages.

RCSB PDB—2BG9: Refined Structure of the Nicotinic Acetylcholine Receptor at 4A Resolution, RCSB Protein Data Bank, retrieved Mar. 17, 2020 from URL: /www.rcsb.org/structure/2BG9, 5 pages.

UniProtKB—P14867 (GBRA1_HUMAN), retrieved Mar. 17, 2020, from URL/www.uniprot.org/uniprot/P14867, 19 pages.

UniProtKB—P62813 (GBRA1_RAT), retrieved Mar. 17, 2020, from URL:www.uniprot.org/uniprot/P62813, 12 pages.

UniProtKB—P28472 (GBRB3-HUMAN), retrieved Mar. 17, 2020, from URLwww.uniprot.org/uniprot/P28472, 21 pages.

UniProtKB—P63079 (GBRB3_RAT), retrieved Mar. 17, 2020 from URLwww.uniprot.org/uniprot/P63079, 11 pages.

Office Action dated May 9, 2020 in Chinese Application No. 201480052000.4 with English translation, 9 pages.

* cited by examiner

A

B

METHODS FOR DETECTING AUTOANTIBODIES AGAINST A GABA(A) RECEPTOR ALPHA 1 SUBUNIT AND/OR BETA 3 SUBUNIT IN AUTOIMMUNE SEIZURE AND/OR ENCEPHALITIS

This application is a National Stage of co-pending PCT/EP2014/072252 filed Oct. 16, 2014, which claims priority to European Patent Application No. 13189172.3 filed Oct. 17, 2013.

SEQUENCE LISTING

The instant application contains a Sequence Listing which has been filed electronically in ASCII format and is hereby incorporated by reference in its entirety. Said ASCII copy, created on Jan. 9, 2018, is named 000174US_SL.txt and is 18,901 bytes in size.

FIELD OF THE INVENTION

The present invention relates to the prognosis, diagnosis and treatment of a newly identified autoimmune disorder, providing a novel cell-surface autoantigen and associated means and methods for detection and treatment of said autoimmune disorder.

BACKGROUND OF THE INVENTION

There is evidence that seizures and status epilepticus can result from immunological responses to excitatory or inhibitory synaptic receptors or proteins that associate to these receptors.[6] These include the N-methyl-D-aspartate receptor (NMDAR), the alpha-amino-3-hydroxy-5-methyl-4-isoxazolepropionic acid receptor (AMPAR), the gamma-aminobutyric acid-B receptor (GABA(B)R), leucine-rich glioma inactivated protein 1 (LGI1), contactin-associated protein-like 2 (Caspr2), and DPPX, a regulatory subunit of the Kv4.2 potassium channels.[21] The epileptic seizures that accompany any of these disorders are often refractory to antiepileptic therapy unless the immune mechanism is identified and treated.[2,15,22] In some patients, seizures or status epilepticus can be the first manifestation of the disease, requiring heavy sedation or prolonged pharmacological coma.[3,17] These treatments may conceal other symptoms such as dyskinesias or psychiatric alterations causing delay in recognizing the disease. Until recently, the main epilepsy-related inhibitory receptor target of autoimmunity was the GABA(B)R.[22] Most patients with GABA(B)R antibodies develop early and prominent seizures or status epilepticus as a component of limbic encephalitis. Approximately 50% of these patients have an underlying small-cell lung cancer (SCLC).[11,16]

Considering that until recently these autoimmune disorders were unknown, the relative high frequency of some has been surprising. For example, in a center focused in the diagnosis and epidemiology of encephalitis (California Encephalitis Project) the frequency of anti-NMDAR encephalitis surpassed that of any individual viral encephalitis.[32] For these reasons, similar immune mechanisms are increasingly being considered in patients who develop rapidly progressive neuropsychiatric symptoms in the context of encephalitis of unknown etiology, a situation that occurs frequently. Nowadays about 70% of encephalitis of unclear etiology remain undiagnosed after extensive evaluation for infectious etiologies.[33] In this setting, the identification of autoantibodies against neuronal cell surface antigens shifts the management to the use of immunotherapy and may extend the intensive care support in cases that otherwise might be considered futile.

In view of the above, the problem underlying the present invention resides in providing means for diagnosis and treatment of a previously unidentified autoimmune encephalitis, or encephalitis of unknown etiology, respectively.

SUMMARY OF THE INVENTION

This problem is solved by the subject matter of the claims, in particular by providing a gamma-aminobutyric acid-A receptor (GABA(A)R), a novel autoantigen implicated in autoimmune diseases, which is for use in a method of prognosis, diagnosis or treatment of an autoimmune disease in a subject, in particular encephalitis, to a cell expressing such GABA(A)R, GABA(A)R fragment or homolog thereof, an antibody binding to said GABA(A)R, GABA(A)R fragment or homolog thereof, to a method for isolating such antibody, to an in vitro prognostic or diagnostic method and test kit involving such GABA(A)R, GABA(A)R fragment or homolog thereof or such cell or antibody, to a pharmaceutical composition comprising such GABA(A)R, GABA(A)R fragment or homolog thereof or such cell, to a medical device coated with such GABA(A)R, GABA(A)R fragment or homolog thereof, such cell, such antibody or such pharmaceutical composition and to methods for treating an autoimmune disorder, in particular encephalitis, in a subject.

While the GABA(B)R, referred to herein above, belongs to the category of metabotropic, G protein-coupled receptors, the GABA(A)R is a ligand gated ion channel that has not been previously recognized as target of autoimmunity. We report here the identification of the GABA(A)R as the target of antibodies from 18 patients comprising two immunological groups: one characterized by high levels of antibodies in serum and CSF occurring in association with prominent seizures or status epilepticus, and the other characterized by low levels of antibodies in serum or absent antibodies in CSF occurring in association with a broader spectrum of symptoms in which the frequency of seizures, opsoclonus, stiff-person syndrome and overlapping autoimmunities is high. In addition, we demonstrate that patient's antibodies specifically alter the levels of synaptic GABA (A)R in cultures of rat hippocampal neurons.

One advantage of the present invention resides in the fact that diagnosis of encephalitis of unknown etiology enables identification of the disease as autoimmune encephalitis, distinction from other (non-autoimmune) forms of encephalitis or other diseases or related symptoms, respectively, and thus provides for specific treatment of the patients with, for example, immunosuppressive agents.

Another advantage of the present invention lies in opening up therapeutical options alternative or in addition to immunosuppression, e.g. by targeting specific autoantibodies.

DETAILED DESCRIPTION OF THE INVENTION

Figure 1:
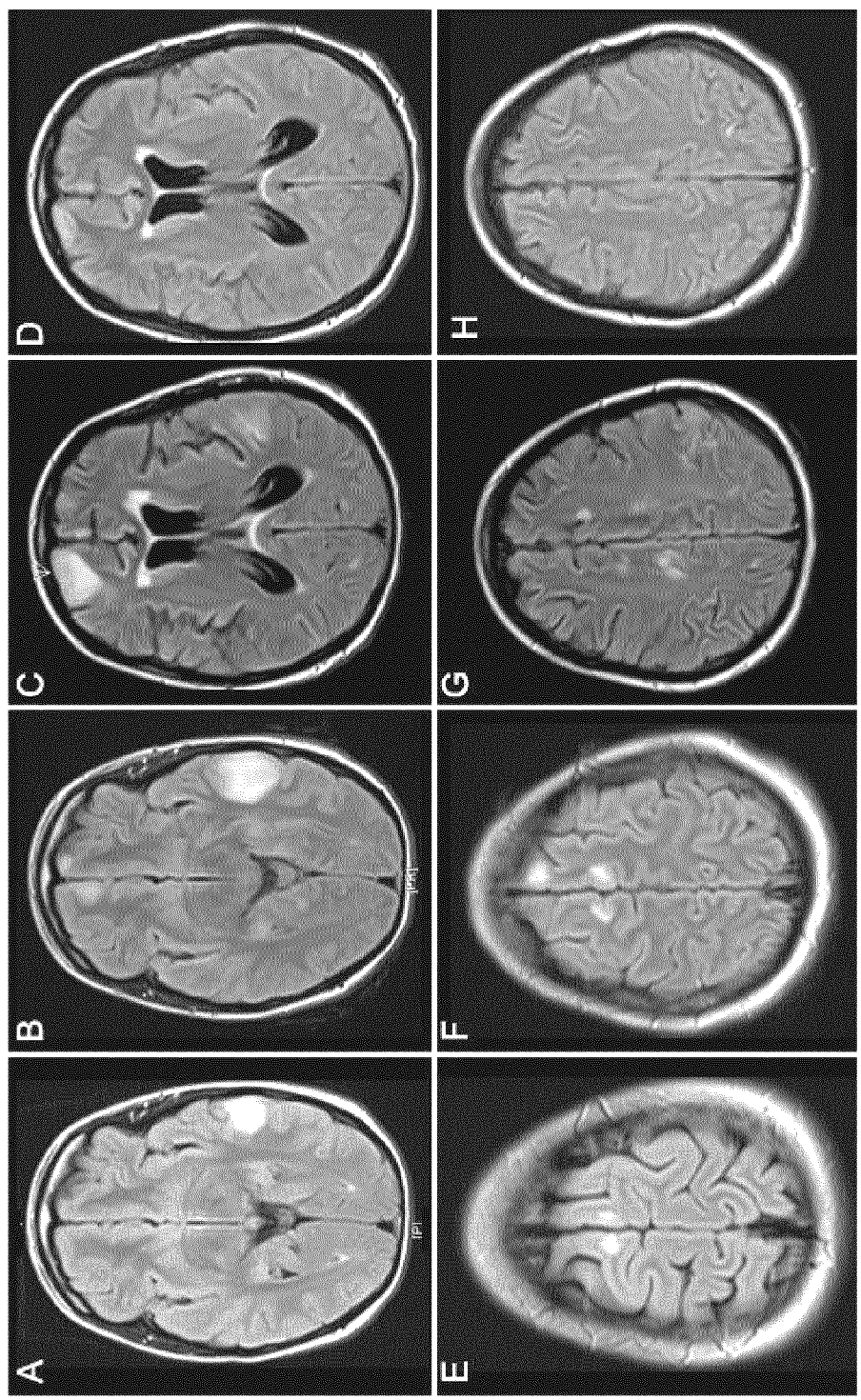
FIG. 1 shows brain MRI images from patient 1.

A "polypeptide", according to the present invention, is understood to be a polymer of two, three, four, five, six, seven or eight or more or up to thousands of amino acids, which may include standard amino acids as well as non standard amino acids. The terms polypeptide, peptide and protein are used interchangeably herein.

The term "fragment", with regard to the polypeptides, peptides and proteins of the invention, refers to a less than full length sequence of said polypeptide, peptide or protein, encompassing e.g. an amino acid sequence which is truncated at one or both termini by one or more amino acids. Alternatively or in addition, such peptide sequence may comprise internal deletions of one or more amino acids. Thereby the residual length of the fragment equals or exceeds the length of one or more continuous or conformational epitopes. When relating to a complex comprising more than one polypeptide, peptide or protein, the term "fragment" refers to a complex with only a subset of its constituents, meaning that the number of the polypeptides, peptides or proteins i.e. the subunits constituting the complex is reduced and/or that one or more of the subunits in the complex is terminally truncated and/or bearing internal deletions as described above.

The term "homolog", with regard to the polypeptides, peptides and proteins of the invention, is understood to relate to a polypeptide, peptide and protein, which exhibits one or more deviations in the amino acid sequence compared to the original sequence. Those deviations may be exchanges or insertions of one or more amino acids or protein motifs or protein domains. For example, a homolog may have at least 70, 75, 80, 90, 92, 94, 96, 98 or 99% sequence identity to the respective original sequence. Alternatively, the stretch of homology may be restricted to 7, 8, 9, 10, 11, 12, 20, 25, 30, 40, 50, 60, 70, 80, 90, 100 or more amino acids of the original sequence. Also in such case, e.g. in case of homology of a single protein domain or motif in the context of a larger non-homologous protein, the homolog may have at least 70, 75, 80, 90, 92, 94, 96, 98 or 99% sequence identity to the respective original sequence. When relating to a complex comprising more than one polypeptide, peptide or protein or fragments thereof, the term "homolog" refers to a complex with at least one of its subunits being replaced by a homolog as described herein above.

The term "autoimmune disease", with regard to the present invention relates to diseases in association with antibodies against a GABA(A)R. As reported herein below, patients exhibiting such autoimmune disease suffer from symptoms including Memory problems, confusion, fatigue, lethargy, social anxiety, behavioral changes, psychosis, depression, mutism, cognitive dysfunction, nausea, vertigo, scintillating scotomas, headache, seizures, epilepsia partialis continua, status epilepticus, opsoclonus, opsoclonus-myoclonus, stiff-person syndrome, dystonic movements of the tongue, chorea affecting the limbs and trunk, progressive hemiparesis, ataxia, chorea affecting the limbs and trunk. These symptoms primarily affect the nervous system and, more specifically, are at least in part associated with defects in the central nervous system. Therefore, the autoimmune disease according to the invention may be an autoimmune encephalitis.

An "epitope", within the scope of the present invention, is understood to be a fragment of one or several proteins which can be specifically recognized (i.e. bound) by an antibody. The epitope may be a conformational epitope, composed of discontinuous sections from a single protein's amino acid sequence or discontinuous sections derived from several different proteins, or a linear epitope, composed of a continuous section of certain length from a single protein's amino acid sequence. For example, linear MHC class I epitopes are about 8 to 11 amino acids in length. In addition to the above the term "epitope" also encompasses epitopes derived from the original sequence of the protein or proteins.

The term "derived", with regard to epitopes, within the scope of the present invention relates to epitopes formed from discontinuous or continuous sections of the primary amino acid sequence of a polypeptide or protein. It is known in the art, that one or more amino acids in epitopes may be replaced e.g. by conservative amino acid replacement (e.g. glutamate to aspartate E→D, glutamine to asparagines Q→N, phenylalanine to tyrosine F→Y, leucine to isoleucine L→I) substantially without changing antibody-binding strength or specificity. Accordingly, the term "derived" relates also to such epitopes that, while featuring differences in the amino acid sequence, exhibit an unchanged or substantially unchanged or enhanced antibody-binding strength or specificity when compared to epitopes with the original amino acid sequence.

"Nucleic acid", according to the present invention, relates to a DNA or RNA polymer including also chemical derivatives thereof or synthetic analogs such as Peptide nucleic acids or Morpholino nucleic acids. It is known in the art that, due to the degeneration of the genetic code, certain changes of the nucleic acid code do not result in changes of the peptide sequence encoded therein. Accordingly, the term "nucleic acid" also encompasses nucleic acid sequences differing in sequence from the original nucleic acid sequences as long as coding for the same peptide sequence, e.g. sequences with a codon usage optimized for expression in certain expression systems.

A "vector" according to the present invention is understood to be a circular or linear nucleic acid sequence including an insert, for example a gene or nucleic acid sequence encoding a desired protein, and other features such as sequences required for vector replication, expression of the insert, positive selection of vector bearing host cells or the expression of marker proteins. Such vectors and sequences are extensively known from the prior art.

A "cell" within the scope of the present invention is any prokaryotic or eukaryotic host cell capable of being transformed with a vector. For example, a cell may be a bacterial cell such as an *Escherichia coli* cell or a eukaryotic cell such as an immortalized human culture cell. One example for an immortalized human culture cell is a HEK293 cell.

A "subject" within the scope of the present invention is a mammal, in particular a human.

The terms "gamma-aminobutyric acid-A receptor", "GABA(A) receptor" "GABA$_A$R" or "GABA(A)R" relate to the receptor including all its known subunits and subunit combinations. The GABA(A)R, as mentioned in the outset, is a ligand gated ion channel, which responds to the inhibitory neurotransmitter gamma-aminobutyric acid. As will be discussed herein below in greater detail, the receptor is comprised of 5 subunits which originate from eight gene families that encode for 19 different known subunit types. The GABA(A)R occurs in neural tissue, primarily in the central nervous system and the spinal cord. It can be found also in the peripheral nervous system, for example in motor neurons. The most abundant subunits are alpha- and beta-type subunits, which are mandatory constituents of any GABA(A)R. The GABA(A)R is highly conserved so that even GABA(A)R from species only distantly related to human is suitable for eliciting specific binding by human anti-GABA(A)R antibodies. This holds true for subunits of the GABA(A)R. As mentioned herein above, for example, linear MHC class I epitopes are about 8 to 11 amino acids in length. Hence, in a GABA(A)R homolog already regions of between 8 to 11 amino acids in length, conserved between the respective species and human, are in principle sufficient to elicit specific binding by human anti-GABA(A)R antibodies. In this connection, conserved sequences making up a conformational epitope may be even shorter. Accordingly, "GABA(A)R", "$GABA_AR$" or "GABA(A)R" with regard to the present invention relates to any known isoforms of the protein subunits of GABA(A)R originating from vertebrates, preferably mammals or more preferably Homo sapiens.

The present inventors have identified GABA(A)R as target antigen of autoimmune encephalitis. 18 patients with antibodies against GABA(A)R are described and it is demonstrated that patient's antibodies remove GABA(A)R from synaptic sites. These findings are important because high titers of antibodies are usually associated with prominent seizures and refractory status epilepticus that require pharmacologically-induced coma, while low titers may occur with seizures, opsoclonus-myoclonus, or stiff-person syndrome, frequently accompanying antibodies against other gabaergic proteins (GAD), or TPO suggesting propensitiy to autoimmunity.

Five sets of experiments, discussed in greater detail in the examples herein below, establish the GABA(A)R as a relevant autoantigen in patients with high levels of antibodies in serum and CSF: 1) direct immunoprecipitation of the receptor by patient's antibodies, 2) specific immunostaining of HEK cells expressing the alpha 1 and/or beta 3 subunits of the GABA(A)R with patient's antibodies, 3) abrogation of patient's antibody reactivity with brain neuropil after immunoabsorption with alpha 1/beta 3 subunits of the GABA(A)R, 4) competition of patients' antibodies for the same GABA(A)R epitopes, and 5) demonstration that patient's antibodies cause selective removal of synaptic GABA(A)R, without affecting gephyrin (the scaffold protein that anchors the receptor at post-synaptic sites).

The majority of fast inhibitory neurotransmission in the mature brain is mediated by ligand-gated GABA(A)R.[29] These receptors are pentamers whose five subunits originate from eight gene families that contain multiple isoforms (alpha 1-6, beta 1-3, gamma 1-3, delta, epsilon, theta, pi and rho 1-3). The subunit composition of the receptor governs the intrinsic properties of the channel such as affinity for GABA, receptor conductance, kinetics, and modulation.[10] These 19 subunits can combine in many different ways to form functional receptors, but most receptors at synaptic sites contain two alpha subunits (alpha 1-3 iso forms), two beta subunits, and a gamma subunit arranged in the order gamma-beta-alpha-beta-alpha. In contrast, the receptors located at perisynaptic or extrasynaptic sites are mainly composed of alpha 4 or alpha 6 subunits combined with beta and delta subunits.[31] The antibodies identified in the serum and CSF of all 18 patients reacted with cells co-expressing alpha 1/beta 3 subunits, and when the reactivity with individual subunits could be assessed, the alpha 1 was always recognized by the CSF. Using cultures of rat hippocampal neurons, patient's CSF antibodies produced a decrease of the density of GABA(A)R specifically located at synaptic sites. The total density of GABA(A)R, including synaptic and extrasynaptic receptors was not affected, suggesting a relocation of receptors from synaptic to extrasynaptic sites. This is in contrast with the effects of antibodies associated to other autoimmune encephalitis, such as anti-NMDAR or AMPA receptor encephalitis in which the decrease of the corresponding receptors occurs at synaptic and extrasynaptic sites.

Four dominant mutations in the alpha 1 subunit of the GABA(A)R associate with generalized epilepsy; in vitro studies have demonstrated that each of these mutations results in a substantial loss of alpha 1 subunit function or levels of expression.[31] In addition, mutations of the beta 3 subunit have also been reported in children with absence epilepsy.[28] In line with these findings a frequent feature of the patients with high titer of serum and CSF antibodies against the alpha 1/beta 3 subunits of GABA(A)R was the frequent development of seizures, status epilepticus, or epilepsia partialis continua. Other symptoms, including altered behavior and cognition, confusion, or focal neurological deficits, and the presence of CSF pleocytosis or oligoclonal bands were similar in most respects to those occurring in other forms of encephalitis either viral or immune mediated.[9]

In the group of patients with low titers of antibodies in serum or absent antibodies in CSF, seizures occurred in 50% of the cases. All patients with a clinical picture of non-focal encephalitis developed seizures; the youngest patient (a 3-year old child) required pharmacologic induced coma for refractory status epilepticus. In this group the frequent presence of other relevant autoimmunities could explain the broader spectrum of symptoms. Indeed two of the 4 patients with stiff-person syndrome (a disorder that occurs in association with autoantibodies against other inhibitory receptors or associated proteins) had coexisting GAD65 antibodies, and another patient had NMDAR antibodies which drove the clinical picture (typical anti-NMDAR encephalitis). Interestingly, the CSF of the patient with anti-NMDAR encephalitis showed high titer of NMDAR antibodies, but did not reveal GABA(A)R antibodies. In said patient GABA(A)R antibodies were only identified in serum, suggesting different compartmentalization of the immune responses. In addition, two findings are remarkable, 1) the identification of opsoclonus-myoclonus in 2/12 (17%) patients of the low titer group (3/18 [17%] of the entire series), which makes the GABA(A)R one of the most common neuronal antigens reported in patients with opsoclonus-myoclonus, and 2) the unexpected number of cases with anti-GAD associated encephalitis or seizures (3/5, 60%, in the low titer group) compared with other more frequently recognized anti-GAD associations (e.g., stiff-person syndrome) which occurred in 2/4 (50%) of cases. These findings emphasize that in patients with encephalitis or seizures attributed to GAD antibodies the presence of more relevant antibodies against cell surface or synaptic proteins, such as the GABA receptors, should be considered.[4,24] Increasing numbers of patients previously characterized as Hashimoto's encephalitis due to the detection of TPO antibodies in the context of encephalitis of unclear etiology are found to have other disorders.[8,22] In the current study 4/18 patients (22%) had TPO antibodies.

Most of the patients with GABA(A)R antibodies and seizures had an abnormal EEG that frequently showed multifocal epileptic activity, and in two cases generalized periodic discharges. These findings were associated with extensive brain MRI abnormalities in 6/6 (100%) patients with high titer serum GABA(A)R antibodies (all with CSF antibodies), and in 3/12 (25%) patients with low antibody titers. These MRI abnormalities predominantly involved cortical and subcortical regions; however, the involvement of basal ganglia, brainstem or cerebellum in a few patients suggests that any area of the brain can show radiological abnormalities. Therefore, compared with patients with other types of antibody-associated encephalitis, those with antibodies to GABA(A)R and seizures show more often extensive and diverse brain MRI abnormalities. As an example, only 30% of the patients with anti-NMDAR encephalitis have initial MRI abnormalities (usually transient and less extensive),[28] and most patients with AMPAR,[19] GABA(B)R,[11,16] or LGI1 antibodies[14,20] have abnormal MRI findings highly restricted to medial temporal lobes, consistent with typical limbic encephalitis.

Comparison with other types of autoimmune synaptic encephalitis shows several additional differences. Thirty nine percent of patients with GABA(A)R antibodies are younger than 18 years, while most of the other types of encephalitis (except anti-NMDAR) occur in adults and elder individuals.[21] Moreover, patients with GABA(A)R antibodies rarely had an underlying tumor, whereas in some other encephalitis (AMPAR, GABA(B)R) about 50% of the patients had a tumor,[23] or in the case of anti-NMDAR encephalitis the frequency of a tumor varies according patients' age and gender.[28]

There is evidence that status epilepticus and other forms of brain injury may lead to chronic epilepsy. The development of chronic epilepsy is usually preceded by a silent period during which there is increasing hyperexcitability in association with a progressive decrease of the clusters of synaptic GABA(A)R.[10] This effect has been attributed in part to a disruption of the GABA(A)R-anchoring protein, gephyrin.[10,25] These data and the antibody-mediated decrease of synaptic GABA(A)R reported here suggest a model whereby the receptors are removed from synapses by patient's antibodies leading to seizures and status epilepticus which in turn would lead to a further decrease of receptors resulting in a pathogenic reinforcement. This would explain the severity and refractoriness of the seizures associated with high levels of GABA(A)R antibodies in serum and CSF. Despite this, 9/12 assessable patients had partial or complete response to immunotherapy (7), symptomatic therapy (2) and prolonged intensive care support.

A prospective assessment of patients to better characterize the high versus low titer groups is important, as well as to assess the CSF of all patients, including those with opsoclonus-myoclonus and stiff-person syndrome. In addition, prompt and more aggressive immunotherapy is likely to lead to better outcomes.

Overall, the presence of GABA(A)R antibodies should be considered in patients with (1) severe seizures or status epilepticus of unclear etiology, associated with MRI and CSF findings suggesting an inflammatory process, (2) subgroups with patients with opsoclonus-myoclonus or stiff-person syndrome, (3) any of the above with GAD or TPO antibodies, or other features suggesting a propensity to autoimmunity. Future studies should prospectively determine the incidence of GABA(A)R autoimmunity among patients with new onset seizures or status epilepticus of unclear etiology, and opsoclonus-myoclonus. In addition, it is plausible that patients with stiff-person syndrome and GABA(A)R antibodies may respond better to immunotherapy than patients with antibodies to GAD65 (an intracellular protein). Our finding that patient's antibodies specifically eliminate GABA(A)R from synapses, provide a useful reagent (purified IgG antibodies) to determine how selective disruption of these receptors lead to neuronal hyperexcitability, seizures, chronic epilepsy, or opsoclonus.

Against this background, the present invention provides a GABA(A)R, GABA(A)R fragment, or homolog thereof for use in a method of prognosis, diagnosis or treatment of an autoimmune disease in a subject. Homologues according to the present invention include homologues of the GABA(A)R as well as homologues of the GABA(A)R fragments or subunits mentioned herein. In this connection, it is understood that GABA(A)R, GABA(A)R fragment, or homolog thereof may comprise a mixture of subunits, homologs or protein fragments originating from different organisms or, more generally, may comprise a mixture of homologs and non-homologs. Preferably, the GABA(A)R, GABA(A)R fragment, or homolog thereof comprises at least one human GABA(A)R subunit, more preferably two or more GABA(A)R subunits. In this connection, two subunits which occur at neighboring positions inside GABA(A)R in human tissues may be bound by autoantibodies more strongly than single subunits because of forming conformational epitopes spanning surfaces from both subunits.

In addition, the present invention provides a cell for use in a method of prognosis, diagnosis or treatment of an autoimmune disease in a subject characterized in that the cell expresses a GABA(A)R, GABA(A)R fragment or homolog thereof. The cell according to the invention may either constitute a cell, which has been isolated from an organism but has not been genetically modified, or a cell which has been genetically modified. Preferably, the cell for use according to the invention is a eukaryotic cell. More preferably, the cell is a cell of neural origin or a cell which has been artificially induced to assuming neural fate, such as a somatic cell or adult stem cell. According to another embodiment of the invention, the cell has been genetically altered by transfection, preferably, the cell has been transfected in order to express or overexpress a GABA(A)R, GABA(A)R fragment, or homolog thereof according to the invention. Such cell may constitute a diagnostic means for the detection of the binding of an antibody to the GABA(A)R, GABA(A)R fragment, or homolog thereof e.g. by presenting the GABA(A)R, GABA(A)R fragment, or homolog thereof on its surface.

According to an embodiment of the present invention, the GABA(A)R, GABA(A)R fragment, or homolog thereof for use or cell for use according to the invention, are characterized in that said GABA(A)R, GABA(A)R fragment, or homolog thereof comprises a sequence according to SEQ ID NO: 1, SEQ ID NO: 2 and/or SEQ ID NO: 5.

SEQ ID NO: 1 corresponds to the human GABA(A)R subunit alpha 1 while SEQ ID NO: 2 corresponds to the human GABA(A)R subunit beta 3 and SEQ ID NO: 5 corresponds to the human GABA(A)R subunit gamma 2.

In this connection, according to a preferred embodiment the GABA(A)R, GABA(A)R fragment or homolog thereof according to the invention, comprises one or more alpha 1 subunits, one or more beta 3 subunits and/or one or more gamma 2 subunits.

In another embodiment, the GABA(A)R, GABA(A)R fragment or homolog thereof comprises a sequence having at least 70%, at least 75, at least 80, at least 90, at least 92, at least 94, at least 96, at least 98 or at least 99% sequence identity to the sequences according to SEQ ID NO: 1, SEQ ID NO: 2 and/or SEQ ID NO: 5.

In yet another embodiment, the invention relates to one or more fragments of the GABA(A)R, said fragments comprising at least 7, 8, 9, 10, 11, 12, 20, 25, 30, 40, 50, 60, 70, 80, 90, 100, 200 or more successive amino acids of the sequences according to SEQ ID NO: 1, SEQ ID NO: 2 and/or SEQ ID NO: 5 or of the sequences having at least 70%, at least 75, at least 80, at least 90, at least 92, at least 94, at least 96, at least 98 or at least 99% sequence identity to the sequences according to SEQ ID NO: 1, SEQ ID NO: 2 and/or SEQ ID NO: 5.

According to a preferred embodiment of the present invention, the GABA GABA(A)R, GABA(A)R fragment, or homolog thereof comprises further amino acids, which are N-terminally or C-terminally attached and facilitate purification of the GABA-A receptor or fragment thereof.

In case of the GABA(A)R or a homolog thereof or in case of the fragment of the GABA(A)R or a homolog thereof is comprised of several polypeptides, peptides or proteins, the additional amino acids may be added to at least one or up to all of the polypeptides, peptides or proteins constituting the GABA(A)R, GABA(A)R fragment or homolog thereof. If additional amino acids are attached to only one polypeptide, peptide or protein in the GABA(A)R, GABA(A)R fragment or homolog thereof, it is preferred that said polypeptide, peptide or protein be an alpha 1 subunit or a fragment of thereof. However, it is also possible that the additional amino acids are added to a different polypeptide, peptide or protein that is bound to the alpha 1 subunit or fragment of thereof by direct or indirect protein-protein interaction. In this connection, e.g. when protein complexes are to be used in methods involving conditions potentially affecting direct or indirect protein-protein interaction, it may be preferable to crosslink the polypeptides, peptides or proteins of the GABA(A)R, GABA(A)R fragment or homolog thereof, including the alpha 1 subunit or fragment of thereof, with each other. Methods for crosslinking proteins are known in the art.

Such additional amino acids may, for example, constitute certain sequences or tags that are specifically recognized by other molecules, preferably proteins, more preferably antibodies. Such tags are extensively known in the art and comprise, for example, flag-tags, myc-tags or strep-tags.

According to another preferred embodiment, the GABA (A)R, GABA(A)R fragment, or homolog thereof or cell according to the invention is linked to a reporter-molecule or a solid phase.

Analogous to the additional amino acids described herein above, at least one or up to all of the polypeptides, peptides or proteins constituting the GABA(A)R, GABA(A)R fragment, or homolog thereof may be linked to the reporter molecule or solid phase. If only one polypeptide, peptide or protein in the GABA(A)R, GABA(A)R fragment, or homolog thereof is linked to the reporter molecule or solid phase, it is preferred that said polypeptide, peptide or protein be an alpha 1 subunit or a fragment of thereof. However, it is also possible that a different polypeptide, peptide or protein, which is bound to the alpha 1 subunit or fragment thereof by direct or indirect protein-protein interaction is linked to the reporter molecule or solid phase. Also in this connection, e.g. when protein complexes are to be used in methods involving conditions potentially affecting direct or indirect protein-protein interaction, it may be preferable to crosslink the polypeptides, peptides or proteins of the GABA(A)R, GABA(A)R fragment or homolog thereof, including the alpha 1 subunit or fragment of thereof, with each other.

A cell according to the invention may be linked to a reporter molecule or solid phase in a way depending on the GABA(A)R, GABA(A)R fragment or homolog thereof expressed therein, e.g. if the GABA(A)R, GABA(A)R fragment or homolog thereof constitutes a fusion molecule including one of the alterations described herein and/or acting as a target for a specific antibody. In addition, a cell according to the invention may be linked e.g. to a reporter molecule or solid phase independently from the GABA(A) R, GABA(A)R fragment or homolog thereof expressed therein, e.g. by binding to antibodies or by chemical cross linking A reporter molecule, within the scope of the present invention, is understood to be a molecule that allows direct or indirect detection of either the absence or presence of GABA(A)R, GABA(A)R fragment, or homolog thereof it is linked to, or the absence or presence of an antibody bound thereto. Many kinds of reporter molecules are known in the art, including for example radioactive labels, fluorescent dyes or proteins (e.g. fluorescine, tetramethylrodamine, green fluorescent protein (GFP)), haptenes (e.g. biotin) or enzymes (e.g. alpha-galactosidase A, luciferase, alkaline phosphatase or horseradish peroxidase, suitable for detection using enzyme convertible dyes). Such reporter molecules may be added to the target-protein either during protein synthesis (inclusion of radioactively labeled amino acids, generation of fusion proteins) or after protein synthesis by chemical coupling.

A solid phase in connection to the present invention relates to any solid substrate, to which a polypeptide can be linked for example by direct or indirect covalent binding or by affinity binding via hydrogen bonds and/or lipophilic interaction. For example, the GABA(A)R, GABA(A)R fragment, or homolog thereof of the present invention may be linked to the material of a microtiter plate, the surface of magnetic beads, a membrane (e.g. a Nitrocellulose or PVDF membrane) or to the solid phase of a chromatography column or sheet.

In addition, the present invention provides an antibody binding to the GABA(A)R, GABA(A)R fragment or homolog thereof according to the invention, wherein the antibody is an autoantibody and/or is for use in a method of prognosis or diagnosis of an autoimmune disease in a subject. According to a preferred embodiment, the antibody according to the invention is in isolated or immobilized form.

The present invention also provides a nucleic acid and a vector encoding a GABA(A)R, GABA(A)R fragment, or homolog thereof according to the invention.

According to a preferred embodiment of the present invention, such nucleic acid or vector is characterized in that said such comprises a sequence according to SEQ ID NO: 3, SEQ ID NO: 4 and/or SEQ ID NO: 6 or a complement thereof.

SEQ ID NO: 3 corresponds to the ORF encoding human GABA(A)R subunit alpha 1 while SEQ ID NO: 4 corresponds to the ORF encoding human GABA(A)R subunit beta 3 and SEQ ID NO: 6 corresponds to the ORF encoding human GABA(A)R subunit gamma 2.

In another embodiment, the nucleic acid or vector according to the invention comprises a sequence having at least 70%, at least 75, at least 80, at least 90, at least 92, at least 94, at least 96, at least 98 or at least 99% sequence identity to the sequences according to SEQ ID NO: 3, SEQ ID NO: 4 and/or SEQ ID NO: 6 or the complements thereof.

In yet another embodiment, the invention relates to a nucleic acid or vector comprising a sequence having at least 7, 8, 9, 10, 11, 12, 20, 25, 30, 40, 50, 60, 70, 80, 90, 100, 200 or more successive bases or, respectively, basepairs of the sequences according to SEQ ID NO: 3, SEQ ID NO: 4 and/or SEQ ID NO: 6 or the complements thereof or of the sequences having at least 70%, at least 75, at least 80, at least 90, at least 92, at least 94, at least 96, at least 98 or at least 99% sequence identity to the sequences according to SEQ ID NO: 3, SEQ ID NO: 4 and/or SEQ ID NO: 6 or the complements thereof.

In a preferred embodiment, the vector according to the present invention is adjusted for expression of the GABA(A)R, GABA(A)R fragment, or homolog thereof according to the invention. In this connection, for expression of the GABA(A)R, a homolog thereof, a the fragment of the GABA(A)R comprised of several polypeptides or a homolog thereof, it is possible to either combine coding sequences for all polypeptides, peptides or proteins constituting the GABA(A)R, GABA(A)R fragment, or homolog thereof on a single vector or to provide a set of different vectors which, e.g. when transferred into a cell or a population of cells, may serve to express the GABA(A)R, GABA(A)R fragment, or homolog thereof including all respective constituents. Of course, it is also possible to express different constituents of the GABA(A)R, GABA(A)R fragment, or homolog thereof in separate cell populations.

In this connection a cell genetically modified to express or overexpress the (A)R, GABA(A)R fragment, or homolog thereof according to the invention may be comprising one or more vectors (e.g. a set of vectors as described above) according to the invention. Such cell may be utilized by methods known in the art to produce copies of the vector or to express the GABA(A)R, GABA(A)R fragment, or homolog thereof according to the invention. In this connection, it is preferred if the cell is a eukaryotic cell, more preferably a mammalian cell, even more preferably a human cell and, most preferably, an immortalized human cell such as a HEK cell.

The present invention also provides an in vitro method for prognosticating or diagnosing an autoimmune disease, comprising the steps:
  a. bringing a liquid sample comprising an antibody from a subject into contact with a GABA(A)R, GABA(A)R fragment, or homolog thereof or with the cell according to the invention or bringing a tissue sample from the subject into contact with an antibody according to the invention, and
  b. detecting the binding of the antibody to the GABA(A)R, GABA(A)R fragment, or homolog thereof, to the cell or to the tissue sample.

Accordingly, the in vitro method according to the invention covers a method in which, in a first step, a liquid sample comprising an antibody from a subject is brought into contact with a GABA(A)R, GABA(A)R fragment, or homolog thereof according to the invention, and, in a second step, the binding of an antibody from the liquid sample to the ABA(A)R, GABA(A)R fragment, or homolog thereof or to the cell according to the invention, i.e. a cell expressing or overexpressing the ABA(A)R, GABA(A)R fragment, or homolog thereof, is detected.

As well, the in vitro method according to the invention covers a method in which, in a first step, a tissue sample from a subject is brought into contact with an antibody of the invention, and, in a second step, the binding of said antibody to said tissue sample is detected.

According to a preferred embodiment, in a step preceding step a described above, a liquid or tissue sample from a subject is provided.

A liquid sample according to the invention may be any body fluid, as long as it contains antibodies. For example a sample may be cerebrospinal fluid (CSF), blood or blood plasma, lymph, insterstitial fluid.

A tissue sample according to the invention may be constituted of single cells or an aggregation of cells either attached to each other directly or through an extracellular matrix. According to a preferred embodiment, the tissue sample is of neural origin, e.g. from the central nervous system, the peripheral nervous system or the autonomic nervous system. Alternatively, the tissue sample may be lymph node tissue.

The binding of an antibody to the GABA(A)R, a fragment of homolog thereof in line with the inventive teachings may be exploited using a variety of detection methods known to the person skilled in the art, for example immunofluorescence microscopy or spectroscopy, luminescence, NMR spectroscopy, radioactivity, chemical crosslinking, surface plasmon resonance, native gel electrophoresis or enzymatic activity. While some of these methods allow for the direct detection of the complex, it is preferred that one of the binding partners, preferably the antibody or, more preferably, a second antibody binding to the antibody, is labeled to the effect that the complex may be detected specifically owing to intrinsic properties of the label, for example fluorescence, radioactivity, enzymatic activity, visibility in NMR or MRI spectra or the like. In a preferred embodiment the diagnosis or prognosis is carried out using a method selected from the group comprising western blot, dot blot, protein microarray, ELISA, line blot, indirect immunofluorescence microscopy. Alternatively, more than one of these methods may be used in a complementary manner for more reliable results.

In a preferred embodiment, the prognosis, diagnosis, methods or test kit in line with the inventive teachings contemplate the use of a line blot. The person skilled in the art is familiar with the experimental setup up of line blots, which is described in the state of the art.[34,35] Briefly, the one or more antigen of interest, in the case of the present invention the GABA(A)R, a fragment of homolog thereof comprising at least part of the alpha one subunit, may be attached to a carrier, for example nitrocellulose membrane, and often in combination with further antigens and controls. The nitrocellulose carrier is subsequently exposed to a patient sample comprising antibodies such as diluted serum. If the sample comprises an antibody binding to the antigen, a complex is formed which may be detected, preferably by incubation with a secondary antibody binding to the constant region of the first antibody, which secondary antibody comprises a detectable label, for example a radioactive isotope, a fluorescent dye or, in a preferred embodiment, an active enzyme fused or linked to the secondary antibody, such as alkaline phosphatase which may be readily assayed using chromogenic substrates followed by simple visual examination. Suitable reagents, devices and software packages are commercially available, for example from EUROIMMUN, Lubeck, Germany.

In another preferred embodiment, the prognosis, diagnosis, methods or test kit in line with the inventive teachings contemplate the use of indirect immunofluorescence. The person skilled in the art is familiar with such techniques and the preparation of suitable samples, which are described in the state of the art.[36,37,38] Briefly, a carrier, such as a cover glass for use in microscopy, is coated with cells or tissue sections comprising the antigen, in the case of the present invention the GABA(A)R, a fragment of homolog thereof comprising at least part of the alpha one subunit. The carrier comprising the antigen is exposed to a patient sample comprising antibodies such as diluted serum. If the sample comprises an antibody binding to the antigen, the resulting complex may be detected, preferably by incubation with a secondary antibody comprising a fluorescent dye such as fluorescein, followed by visual examination using fluorescence microscopy. Suitable reagents, devices and software packages are commercially available, for example from EUROIMMUN, Lubeck, Germany.

Furthermore, a test kit is provided in the context of the present invention, which test kit comprises one or more GABA(A)R, GABA(A)R fragments or homologs thereof, a cell and/or an antibody according to the invention. According to a preferred embodiment, the test kit is for the detection of antibodies and comprises antigens in the form of one or more GABA(A)R, GABA(A)R fragments or homologs thereof or cells according to the invention. In this connection, a test kit may comprise e.g. different single subunits of the GABA(A)R or potentially immunogenic fragments or homologs thereof, or combinations of such compounds. According to an alternative embodiment, a test kit of the invention is for use in detecting the GABA(A)R, GABA(A)R fragments or homologs thereof in a sample, e.g. a tissue sample from a subject, and comprises the antibody of the invention. It is of course possible to provide a test kit useful for detecting antibodies as well as GABA(A)R, GABA(A)R fragments or homologs thereof.

In addition, the present invention provides a pharmaceutical composition comprising a GABA(A)R, GABA(A)R fragment, or homolog thereof and/or a cell according to the invention.

A pharmaceutical composition according to the invention may comprise one or more pharmaceutically active substances in addition to the polypeptide according to the invention. In addition, a pharmaceutical composition according to the invention may comprise one or more pharmaceutical excipients. The pharmaceutical composition according to the invention is particularly useful for binding/absorbtion of antibodies of different classes (IgA, IgG) from a subject's blood or plasma and in particular for extracorporeal treatment of an autoimmune disorder. For example, said pharmaceutical composition may be employed in immunopheresis. In this connection, the present invention also provides a medical device coated with a GABA(A)R, GABA(A)R fragment, or homolog thereof or a pharmaceutical composition according to the invention. For example, said medical device may be a device employed in conventional plasma exchange or immunopheresis and comprising surfaces coming into contact with blood or plasma of the subject to be treated.

In addition, the present invention provides a medical or diagnostic device coated with a GABA(A)R, GABA(A)R fragment, or homolog thereof, with a cell, with an antibody and/or with a pharmaceutical composition according to the invention.

Such medical or diagnostic device may be a device which can be brought in contact with a liquid or tissue sample from a subject, such as a microscopic slide, a cover glass, magnetic bead or other carrier, a microtiter plate or a device for culturing cells therein, e.g. a petri dish or culture plate. According to another embodiment, such a device may be a device used in plasmapheresis or immunopheresis, which device is brought into contact with a patient's plasma to bind and extract autoantibodies. Suitable diagnostic devices such as biochips, microplates for ELISA, line blots or coated beads are commercially available, for example from EUROIMMUN, Lubeck, Germany.

Moreover, the present invention also provides a method for treating an autoimmune disease in a subject, the method comprising the steps of
a. subjecting a liquid sample comprising antibodies from a subject to an in vitro diagnostic method of the invention, and
b. treating the subject with at least one suitable pharmaceutical substance and/or plasma exchange.

A suitable pharmaceutical substance, according to the invention may include a substance modulating, in particular suppressing, a subject's immune system or a specific part thereof. According to a preferred embodiment of the present invention, the suitable pharmaceutical substance may be an immunosuppressant drug such as selected from the group consisting of Rituximab, prednisone, methylprednisolone, cyclophosphamide, mycophenolatemofetil, intravenous immunoglobulin, tacrolimus, cyclosporine, methotrexate and azathioprine.

In addition to the administration of immunosuppressants, the patient may also be treated with suitable pharmaceutical substances for treatment of symptoms and conditions related to or caused by the autoimmune disorder to be treated. According to a preferred embodiment, step b. referred to above therefore includes also the administration of other compounds such as antiepileptic drugs. Such antiepileptic drugs may be selected from the group consisting of clonazepam, phenytoin, lamotrigine, phenobarbital, valproic acid, levetiracetam, carbamazepine, tiagabine, felbamate, pregabalin, primidone and gabapentin.

According to a further preferred embodiment, the immunosuppressants and antiepileptic drugs may be administered to the patient in parallel or in succession.

In addition, the present invention provides a method for treating an autoimmune disease in a subject the method comprising the steps of
a. taking blood or plasma from a subject,
b. bringing the blood or plasma into contact with the pharmaceutical composition or the medical device of the invention in order to remove disease associated antibodies, and
c. readministering the blood or plasma to the subject.

In such a method, e.g. immunopheresis, disease associated antibodies are removed from the subject's plasma by bringing the blood or plasma into contact with the immobilized GABA(A)R, GABA(A)R fragment, or homolog thereof according to the invention. Corresponding methods have been described e.g. for the treatment of a dilative cardiomyopathy based on the sequence of the beta-adrenergic receptor.[39]

According to a preferred embodiment, immunopheresis may be combined with other modes of treatment, for example the administration of immunosuppressive compounds or compounds for the treatment of symptoms associated with the autoimmune disease described herein.

The present invention also provides a method for isolating an antibody binding to a GABA(A)R, GABA(A)R fragment or homolog thereof, the method comprising the steps
a. bringing a sample comprising an antibody binding to a GABA(A)R, GABA(A)R fragment or homolog thereof into contact with the GABA(A)R, GABA(A)R fragment or homolog thereof according to any one of claim 1, 3 or 4 or the cell according to any one of claims 2 to 4,
b. isolating a complex comprising the GABA(A)R, GABA(A)R fragment or homolog thereof and the antibody,
c. dissociating the complex isolated in step c. and
d. separating the antibody from the GABA(A)R, GABA(A)R fragment or homolog thereof or cell.

According to a preferred embodiment, step A is preceded by a further step of providing a sample comprising an antibody binding to a GABA(A)R, GABA(A)R fragment or homolog thereof, e.g. the antibody of the invention. Such sample can be, for example, a liquid sample as mentioned herein above, or e.g. a supernatant from a tissue sample or cell culture.

According to a preferred embodiment of the invention, the autoimmune disease is an autoimmune disease of the nervous system, preferably autoimmune encephalitis. Alternatively, the invention relates to an autoimmune disease of the peripheral or autonomic nervous system.

LEGENDS TO THE FIGURES

FIG. 1: MRI findings in patient #1

On day #3 of admission the MRI of this patient showed multiple cortical-subcortical abnormalities with increased FLAIR/T2 signal involving the left temporal lobe and frontal parasagittal regions (A, E). On day #10, a repeat MRI shows an increase of the size of the temporal lesion and a new cortical lesion in the left frontal lobe (B, F). Repeat MRIs on days #22 and 48 did not show substantial changes (not shown). Another MRI obtained 4 months after disease onset shows numerous new multifocal abnormalities along with diffuse atrophy and increase of the size of the ventricles (C, G). A repeat MRI two months later, 6 months after symptom onset shows substantial improvement and resolution of the abnormalities as well as improvement of the ventricular dilatation (D, H).

Figure 2:
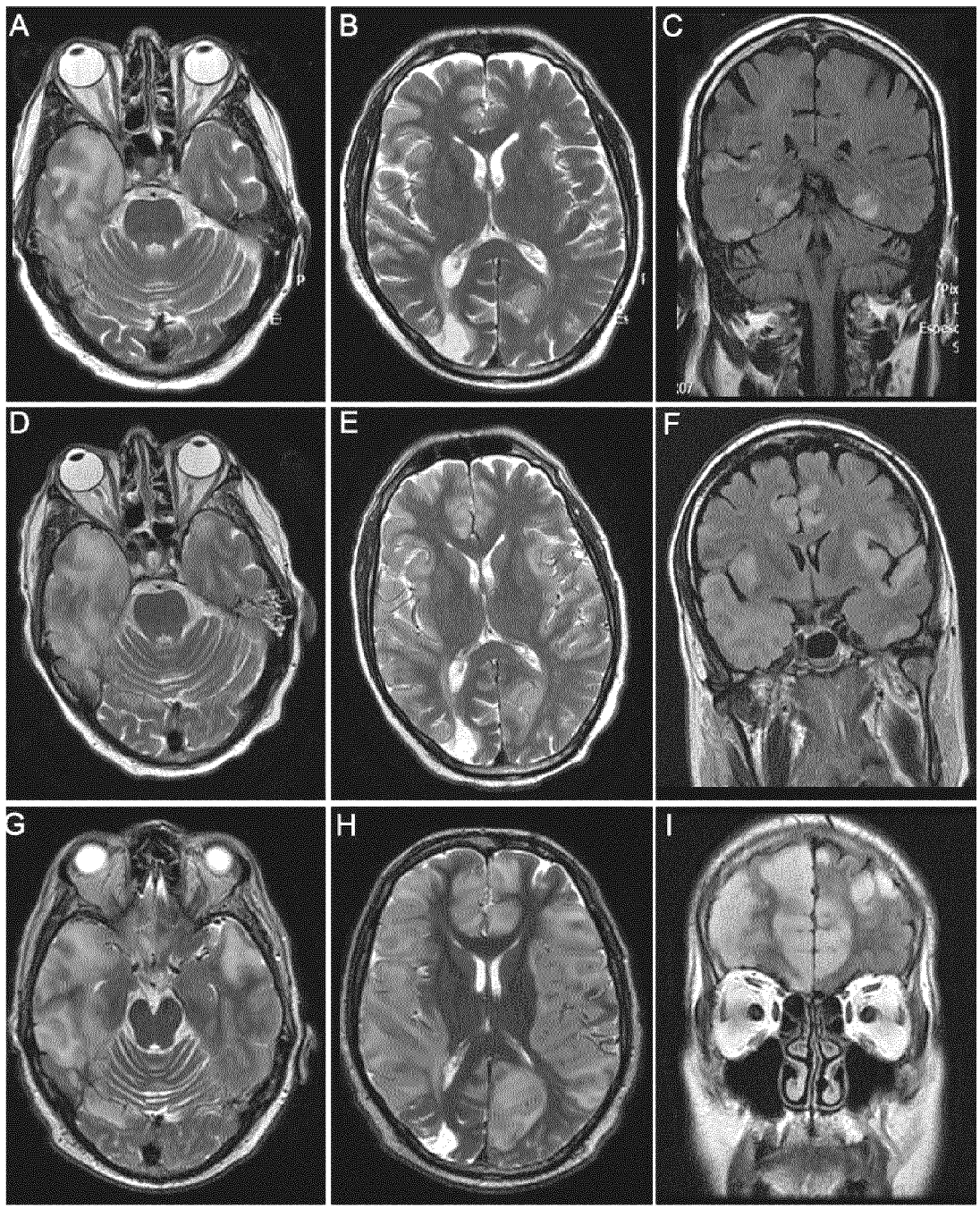
FIG. 2 shows brain MRI images from patient 2.

FIG. 2: MRI findings in index patient #2

On day #2 of admission the MRI of this patient showed multiple areas of FLAIR/T2 signal abnormality predominantly involving cortical regions (A-C), without edema, mass effect, or contrast enhancement (not shown), but with blurring of the grey-white matter junction. On day 14, repeat MRI shows interval increase of the cortical-subcortical involvement, with edema in the right temporal lobe (D-F). Subsequent MRIs showed a marked worsening of these abnormalities now extensively involving cortical and subcortical regions (G-I).

Figure 3:
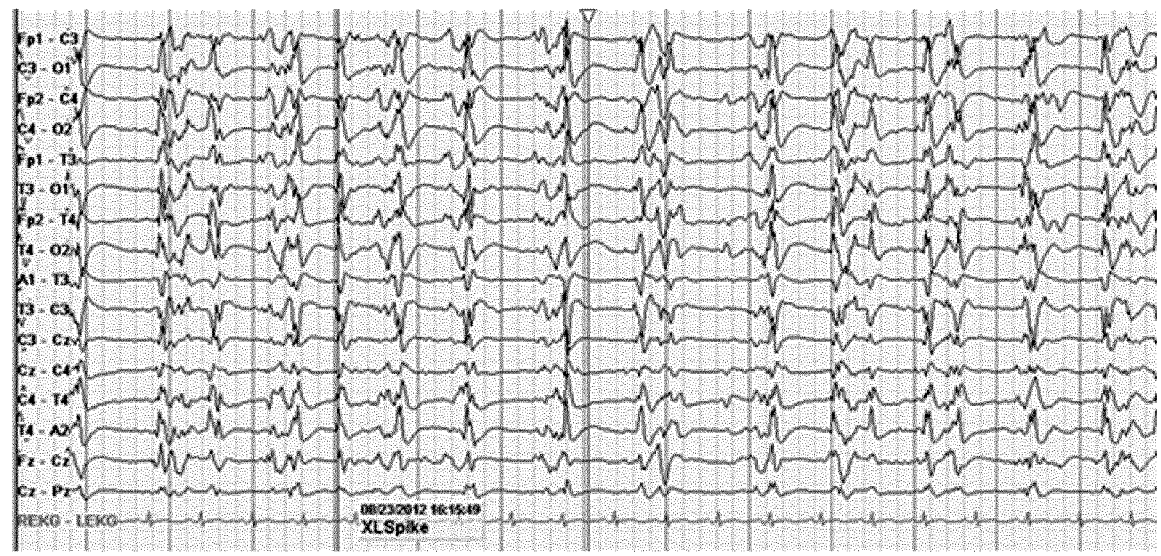
FIG. 3 shows EEG recordings from patients 1 and 2.
Figure 3:

FIG. 3: Generalized periodic discharges in patients with encephalitis and antibodies to GABA(A)R The recording in A corresponds to the EEG of patient #1 obtained one month after admission; note the presence of generalized epileptiform discharges. The recording in B corresponds to patient #2; this patient initially showed epileptiform activity in the right temporal lobe with tendency to generalization in posterior recordings, as shown in B.

Figure 4:
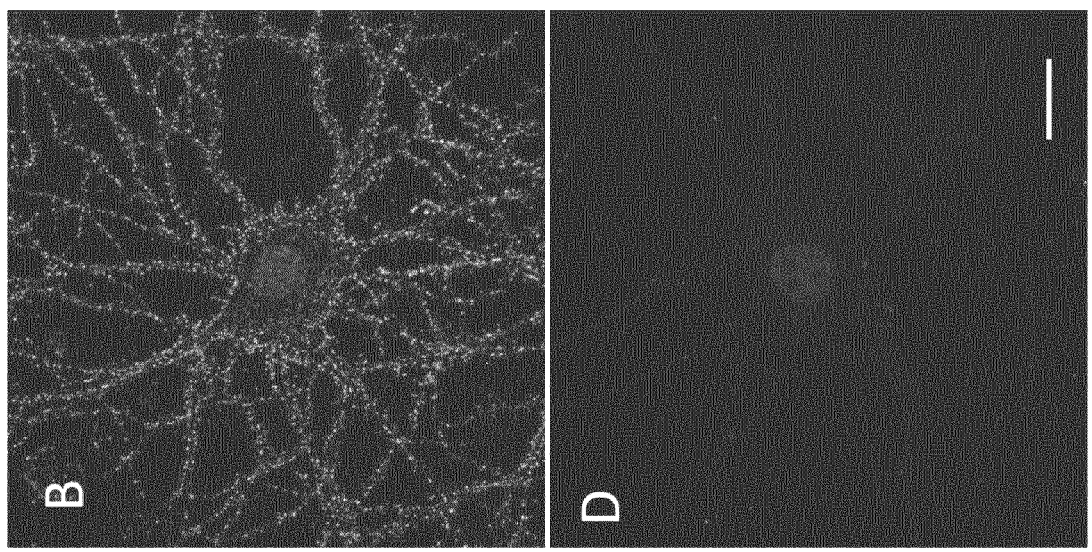
FIG. 4 shows CSF antibody reactivity with rat brain.
Figure 4:

FIG. 4: Reactivity of CSF of a patient with GABA(A)R antibodies with rat brain

The patient's CSF shows extensive and diffuse immunostaining of the neuropil of cortical and subcortical regions (A). This pattern of neuropil reactivity suggested the presence of antibodies against a neuronal cell surface antigen, which was confirmed in cultures of live rat hippocampal neurons (B). Panels C and D show a similar study using CSF of a control individual without GABA(A)R antibodies. In B and D the nucleus of the neurons was counterstained with DAPI. Scale bar in C=2 mm and in D=20 micrometers.

Figure 5:
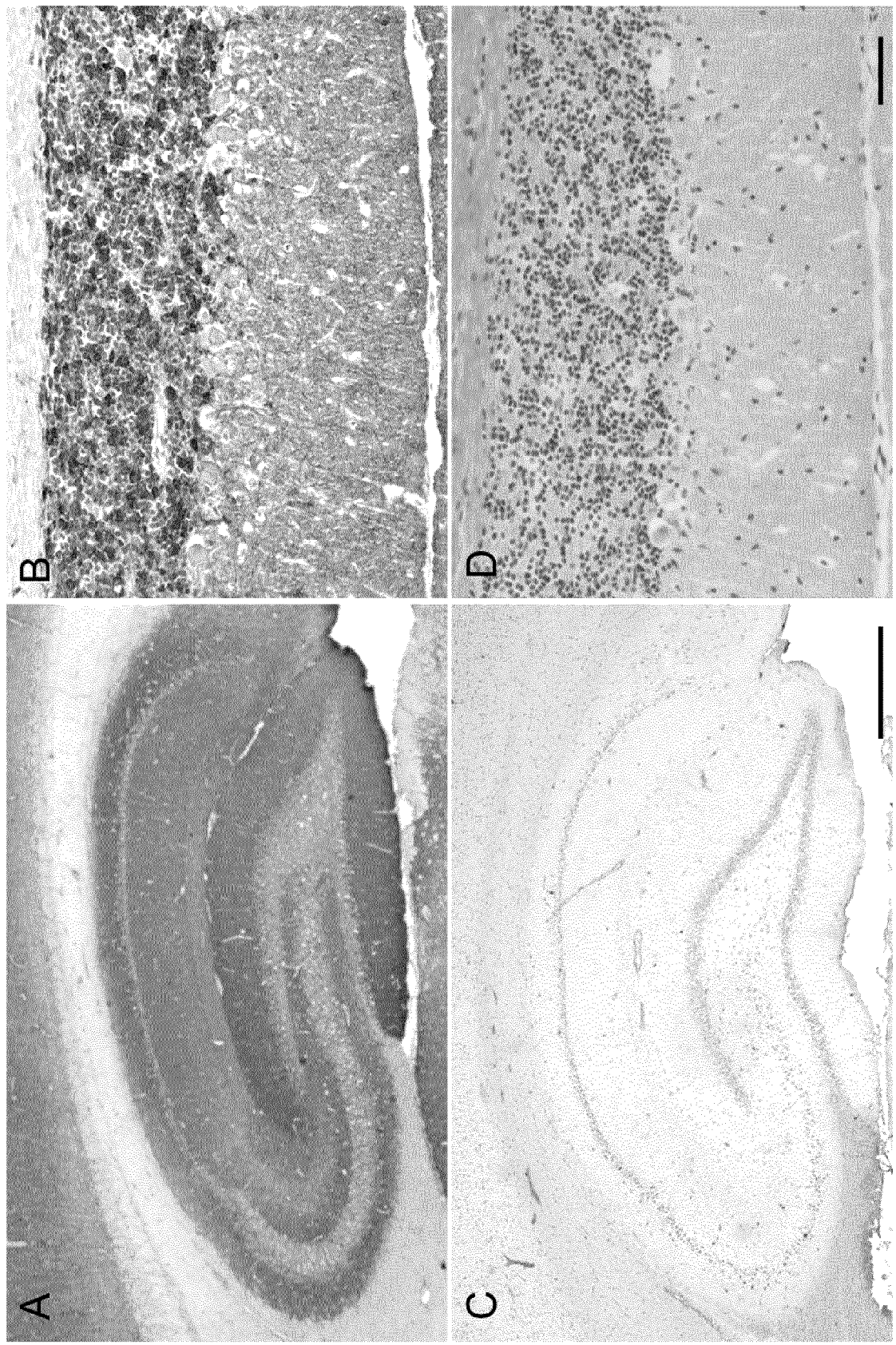
FIG. 5 shows reactivity of patient's CSF with rat hippocampus and cerebellum at high magnification.

FIG. 5: Reactivity of patient's CSF with rat hippocampus and cerebellum shown at high magnification Panels A and B show the reactivity of a patient's CSF (1:4) with rat hippocampus and cerebellum. Panels C and D show the lack of reactivity of a control CSF. Scale bar=500 micrometers.

Figure 6:
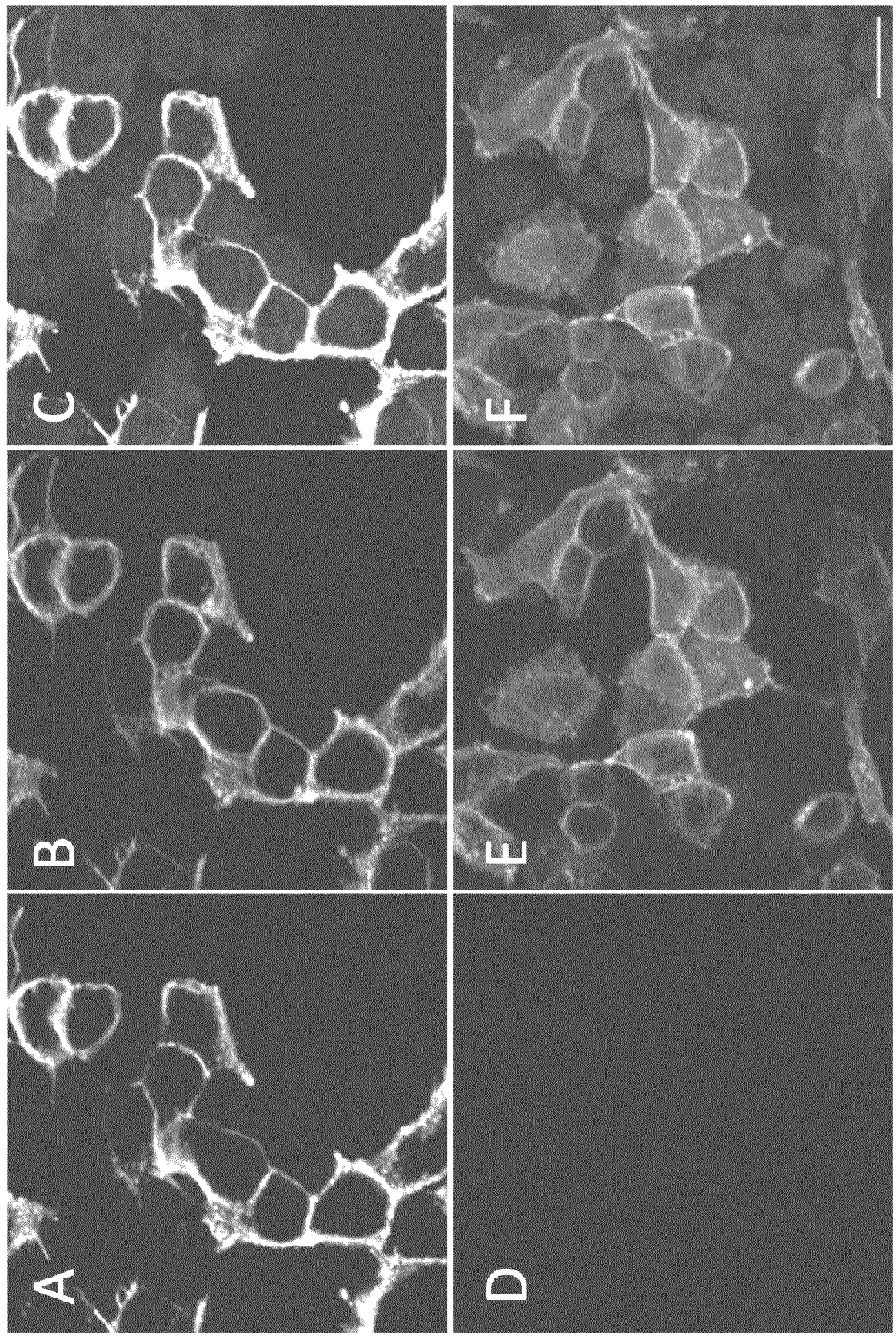
FIG. 6 shows CSF antibody reactivity with GABA(A)R expressing HEK cells.

FIG. 6: Reactivity of a patient's serum with live HEK cells expressing GABA(A)R

Reactivity of live HEK cells expressing human alpha 1 and beta 3 subunits of the GABA(A)R with a patient's serum and a monoclonal antibody against the alpha 1 subunit (B). The merged reactivities are shown in C. A similar assay with serum from a normal individual is shown in (D-F). The nuclei of the cells are shown with DAPI in C and F. Note the specific reactivity of patient's antibodies with cells expressing GABA(A)R and the good co-localization with the reactivity of the commercial antibody. Scale bar=20 micrometers.

Figure 7:
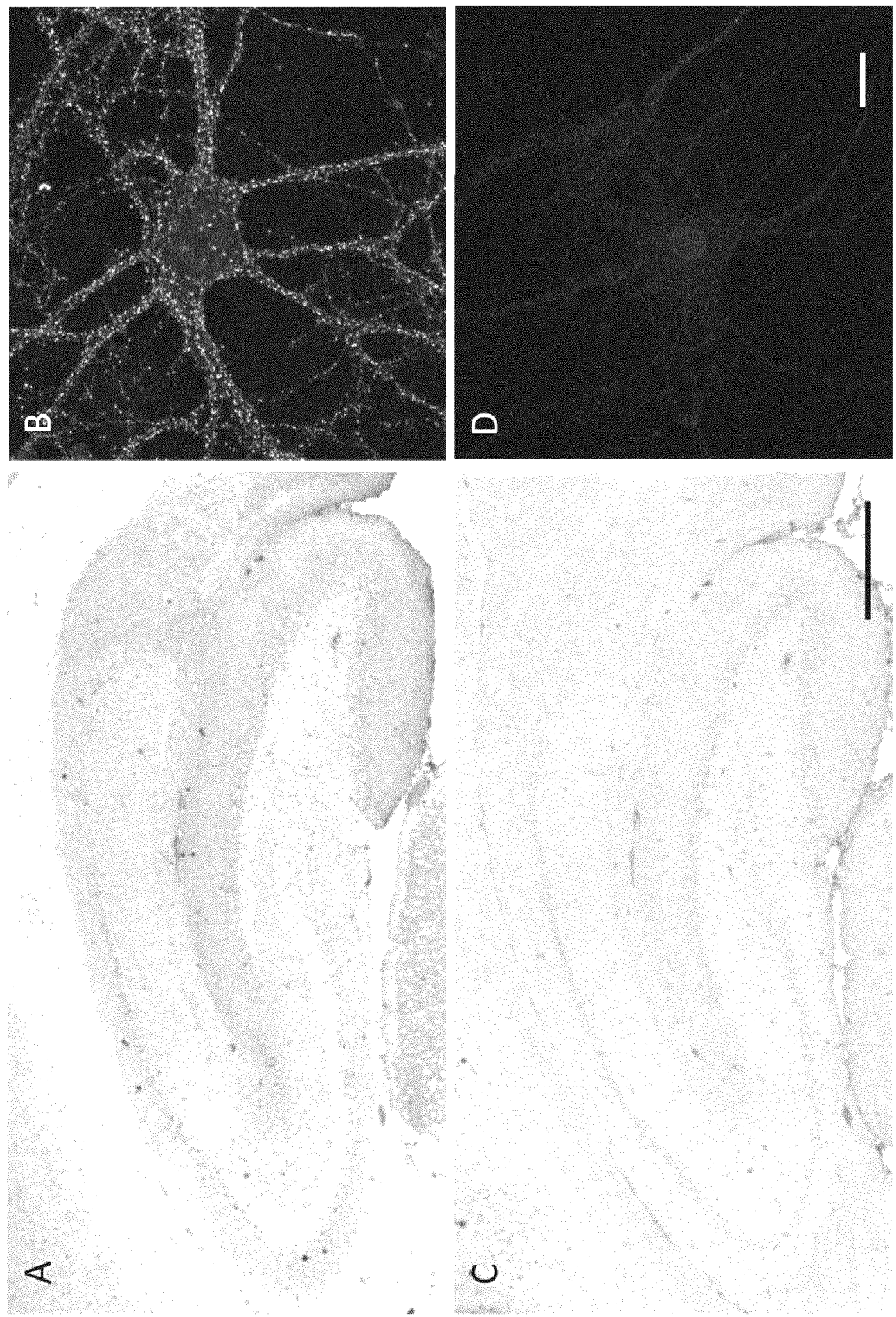
FIG. 7 shows results of immunoabsorption using GABA (A)R expressing HEK cells.

FIG. 7: GABA(A)R immunoabsorption of serum antibody brain and neuronal reactivity Panels A and C show the reactivity of a patient's serum after immunoabsorption with non-transfected HEK cells. Panels B and D show that this reactivity is abolished after the serum has been immunoabsorbed with HEK cells expressing the GABA(A)R. Scale bar in A and C=500 micrometers, Scale bar in B and D=20 micrometers.

Figure 8:
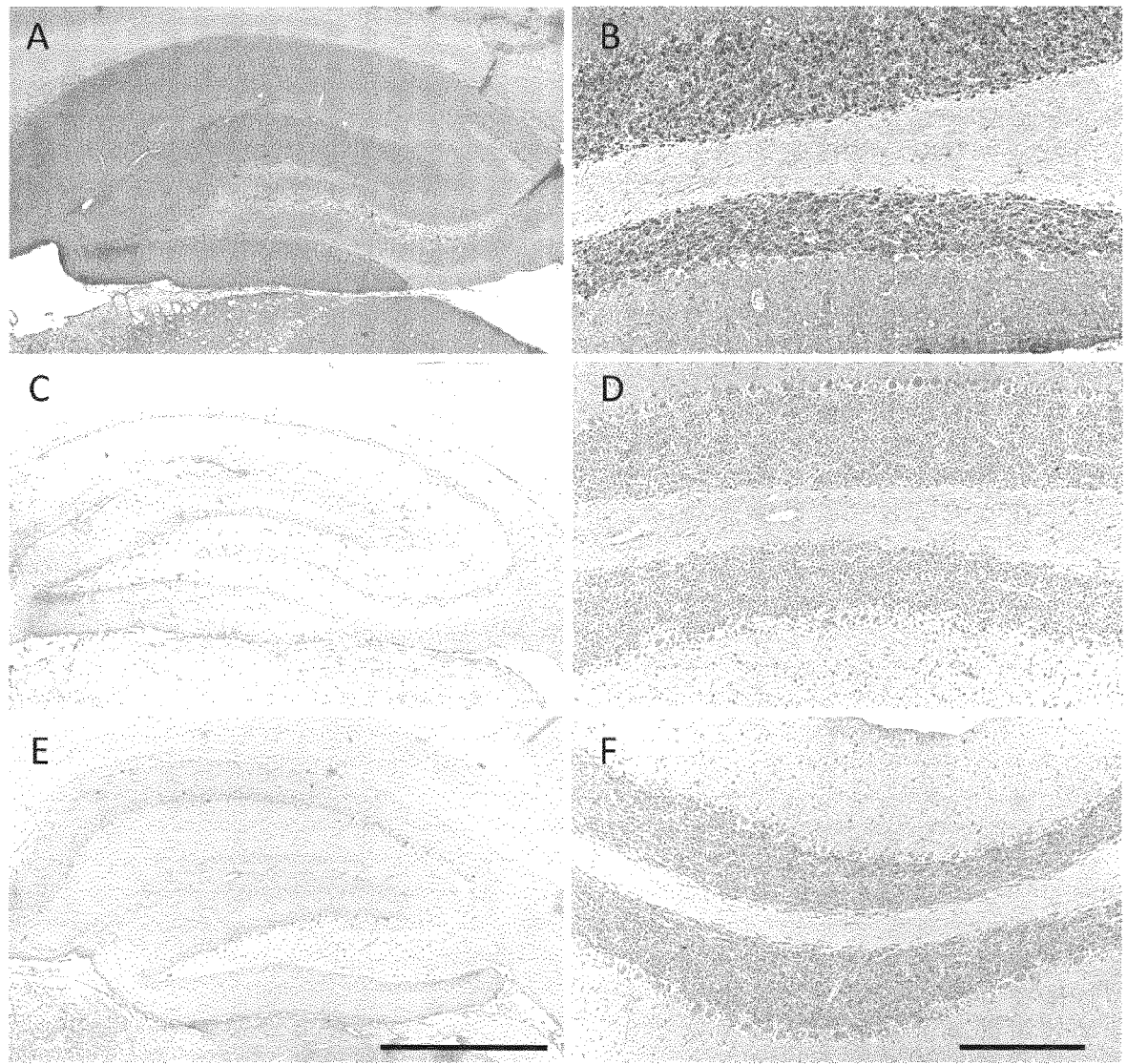
FIG. 8 shows the results of immunocompetition studies with patient's antibodies.

FIG. 8: Immunocompetition studies demonstrating that patients' antibodies recognize the same epitopes of the GABA(A)R Reactivity with rat brain of biotinylated IgG from a patient with GABA(A)R antibodies in which the tissue has been pre-incubated with serum from a normal individual (A and B), the serum from the same patient whose IgG has been biotinylated (C, D), and the serum of another patient with GABA(A)R antibodies. Note the dramatic decrease of reactivity (competition for the same GABA(A)R epitopes) in panels E and F compared with A and B. Panels C and D (competition with same patient's serum serves to demonstrate the background reactivity). Scale bar for A, C, E=1 mm; Scale bar for B, D and E=200 micrometers.

Figure 9:
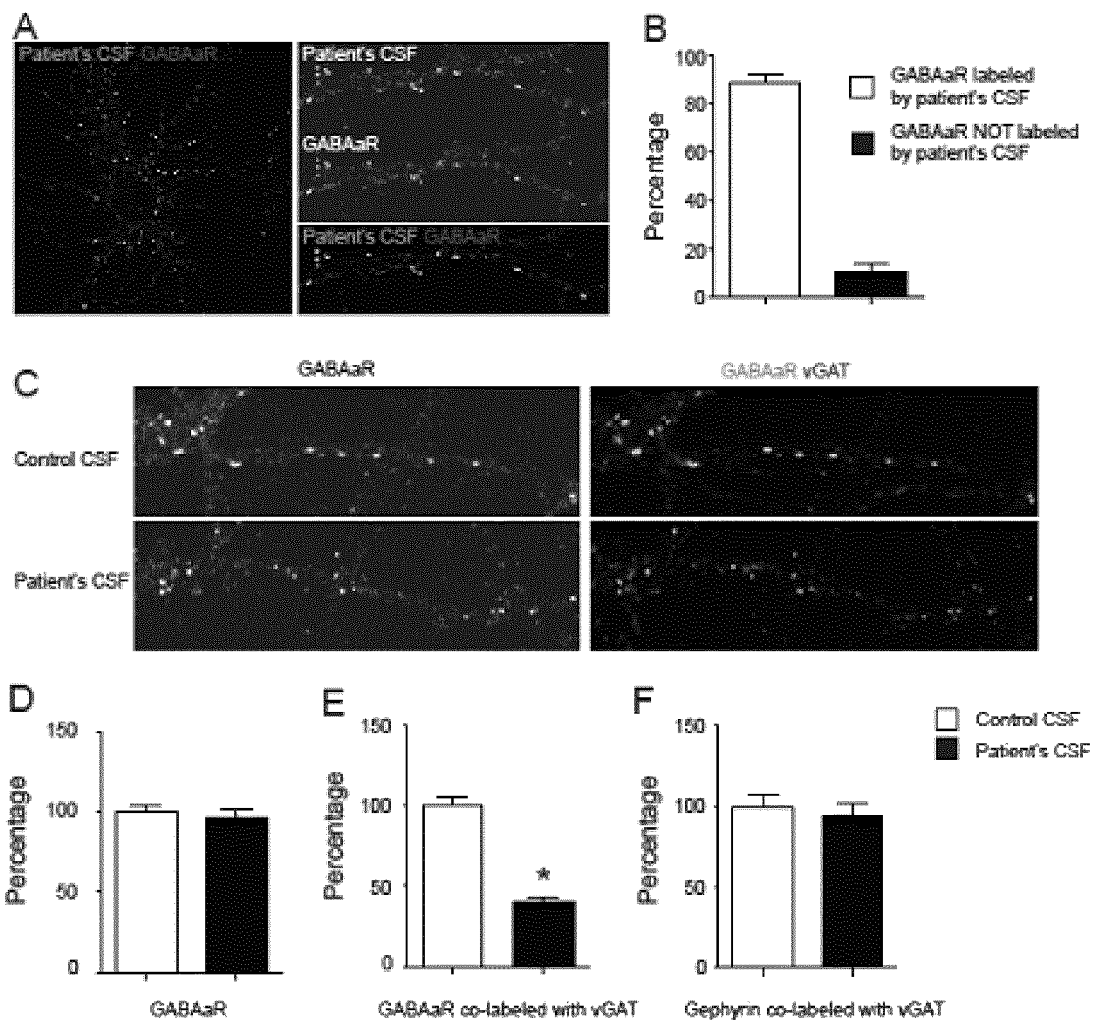
FIG. 9 shows selectivity and effects of patient's antibodies binding the GABA(A)R.

FIG. 9: Patient's antibodies selectively bind GABA(A)R and alter the localization of GABA(A)R in live neurons A) Live 14 div neurons were stained with patient's CSF containing GABA(A)R antibodies (green, right panel, uppermost image), then fixed and stained with commercial GABA(A)R antibodies (red, right panel, middle image). B) Quantification of colocalization between patient's CSF antibodies and the commercial GABA(A)R antibody shows that 89±3% of receptors labeled by patient's antibodies were co-labeled with the commercial antibody against GABA(A)R, and 11±3% were not. C) 14 div neurons were incubated with patient's CSF for 48 hours and subsequently stained for postsynaptic GABA(A)R (green, left panel) and presynaptic vGAT (red, right panel, overlayed with signal from left panel). The synaptic GABA(A)R (shown as yellow puncta in control conditions) were greatly reduced after treatment with patient's CSF.

D) The number of GABA(A)R clusters along dendrites of neurons treated with patient's CSF is not different from neurons treated with control CSF (Mann-Whitney test, p=0.6). E) In contrast, the number of GABA(A)R localized in synapses decreased significantly in neurons treated with patient's CSF compared to neurons treated with control CSF (40%±0.3 compared to control as 100%, Mann-Whitney test, p<0.0001).

F) Patient's CSF did not affect the clusters of gephyrin (post-synaptic) co-labeled with vGAT (pre-synaptic) along a dendrite when compared with the effects of control CSF (Mann-Whitney test, p=0.5).

EXAMPLES

Example 1: Patients

From August 2012 until February 2013, two patients with encephalitis, refractory seizures, and CSF showing a similar pattern of reactivity with cell surface proteins of the neuropil of rat brain were prospectively identified (index patients 1 and 2). The severity of the clinical picture and unknown identity of the antigen prompted us to isolate and characterize it and to retrospectively review the clinical and immunological information of patients with similar features.

From April 2006 until April 2013, the serum and CSF of 1134 patients with encephalitis and seizures suspected to be autoimmune were studied in the Department of Neurology, Hospital of the University of Pennsylvania or in the Service of Neurology, Hospital Clinic, University of Barcelona (currently, Center of Neuroimmunology, Institut d'Investigacions Biomediques August Pi i Sunyer [IDIBAPS]).

Of these 1134 patients, 356 (44%) had serum or CSF antibodies that reacted with known cell surface/synaptic antigens, and 140 had the triad encephalitis, seizures, and antibodies against unknown antigens of the neuropil of rat brain. Serum and CSF of these patients were re-examined for antibody reactivity with similar features to those of the index cases. In addition, serum of 30 normal individuals (blood donors) and serum or CSF of 217 patients with diverse disorders were similarly tested, including 65 with antibodies against glutamic acid decarboxylase 65 (GAD65), 25 with NMDAR antibodies, 21 with GABA(B)R antibodies, 23 with opsoclonus-myoclonus, 12 with LGI1 antibodies, 12 with Hu antibodies, 9 with post-herpes simplex virus encephalitis, 30 with multiple sclerosis, and 20 with non-inflammatory degenerative disorders.

Studies were approved by the institutional review boards of the University of Pennsylvania and the University of Barcelona.

a) Index Case 1

This 16 year-old girl presented to the hospital with a four-day history of severe fatigue and headache, accompanied by vertigo, nausea, and scintillating scotomas. She complained of several months of memory difficulties, cognitive dysfunction, anxiety, depressed mood and fatigue. Her past medical history was significant for Hodgkin's lymphoma which was in remission since completing chemotherapy and radiation 10 months earlier. On the fifth day of admission, she had a generalized tonic-clonic seizure and rapidly progressed to having frequent seizures. Complete blood cell count, C-reactive protein and erythrocyte sedimentation rate were normal. Testing for anti-thyroid peroxidase, anti-thyroglobulin, anti-nuclear antibodies, anti-neutrophil cytoplasmic antibodies, and paraneoplastic antibodies (Hu, Ri, Yo, CRMP5, amphiphysin) were negative. Brain MRI on day 3 demonstrated multiple foci of increased T2/FLAIR signal in both hemispheres (FIG. 1A, E). CSF analysis showed normal opening pressure, 23 white blood cells (WBC)/mm$^3$ (69% lymphocytes), normal cytology, and protein and glucose concentrations. Gram stain, routine cultures and PCR testing for herpes simplex virus, Enterovirus and *Mycoplasma pneumoniae* were negative. Serology for Cytomegalovirus, Epstein-Barr virus, Arbovirus, *Bartonella henselae*, and Lyme disease were negative.

Treatment with high-dose methylprednisolone was initiated on day 7. Very high doses of phenobarbital were required to suppress electrographic seizures. A subsequent course of plasmapheresis on alternating days for one week failed to improve the seizure pattern. On day 10, repeat brain MRI showed increase of the size of the FLAIR/T2 abnormalities, mainly in the left temporal lobe, and multifocal new cortical and subcortical lesions in both cerebral hemispheres (FIG. 1B, F). Brain biopsy on day 14 demonstrated intense diffuse reactive astrocytic gliosis throughout the cortex associated with microglial activation and a population of reactive T lymphocytes. Several days later, antibodies against neuronal cell-surface antigens were identified in her CSF. She received high-dose corticosteroids, intravenous immunoglobulin, rituximab and cyclophosphamide. Phenobarbital coma was continued for four months during which time breakthrough seizures occurred if the phenobarbital level was allowed to decrease. EEG recordings demonstrated generalized periodic discharges late in the first month of admission (FIG. 3, A).

After three months, the EEG showed more focal left-sided epileptiform discharges. The phenobarbital dose was weaned and she began a slow neurological recovery with gradual resolution of the encephalopathic EEG pattern. Four months after admission a repeat lumbar puncture showed resolution of the leukocytosis; however, repeat MRI showed numerous new multifocal lesions throughout the brain with diffuse atrophy and moderate ex-vacuo ventricular dilatation (FIG. 1 C, G). Six months after her initial presentation, she began to show more rapid neurological recovery. Repeat MRI demonstrated no new lesions, improvement or resolution of all previous lesions, and reduction of the previous seen diffuse atrophy (FIG. 1 D, H). She was transferred to an inpatient rehabilitation facility seven months after presentation and over the subsequent three months made significant gains to the point that she was able to communicate, eat, dress and groom herself. She could walk short distances with minimal assistance. Ten months after she first presented, she was discharged home able to carry out most activities of daily living independently.

b) Index Case 2

A 51 year-old man was admitted to the hospital for rapidly progressive symptoms of change of behavior and new-onset psychosis. Prior to admission the patient was seen several times in the emergency department of another hospital where he was diagnosed with new onset depression and treated with sertraline and alprazolam. In addition, he had complained of generalized pruritis and developed worsening high blood pressure. On several occasions the family heard the patient saying he was going to kill other people and himself. A few days prior to admission, he refused to get out of bed, and became apathetic with almost total reduction of verbal output. His past medical history was relevant for high blood pressure, diabetes mellitus, hypercholesterolemia, stroke (from which he had fully recovered), and thrombotic thrombocytopenic purpura treated a few years earlier with splenectomy and steroids.

At admission, the clinical picture resembled akinetic mutism, with brief periods in which the patient spontaneously uttered a few incoherent sentences. The day of admission, he was noted to have clonic seizures involving the left side of the face and left arm that resolved with intravenous diazepam and levetiracetam. Over the next 24 hours he developed acute respiratory failure due to pneumonia, requiring intubation and admission to intensive care unit. Two days later he developed status epilepticus characterized by clonic movements of the left side of the face and left arm, associated with continuous saccadic eye movements to the left that were refractory to all treatments, including levetiracetam, lacosamide, and phenytoin. The patient was maintained in a pharmacological coma, sequentially using midazolam, propofol, and thiopental. The seizures persisted until the patients' death 10 weeks after presentation.

The initial EEG showed epileptiform activity in the right temporal lobe with a tendency to generalization that in subsequent recordings progressed to a pattern of generalized periodic wave activity (FIG. 3, B). The MRI showed multiple increased FLAIR/T2 signal abnormalities, extensively involving cortex without mass effect or contrast enhancement, blurring the grey-white matter junction (FIG. 2 A-C). The initial CSF study was normal, but a repeat CSF analysis several days later showed IgG and IgM oligoclonal bands without matching serum bands. The following tests were negative: 1) Blood infectious disease studies for syphilis, hepatitis virus B and C, *Brucella melitensis, Borrelia burgdorferi, Toxoplasma gondii, Streptococcus pneumonia*, and *Legionella pneumophila;* 2) CSF studies for bacterial and fungal infections, herpes simplex virus 1 and 2; human herpesvirus 6, cytomegalovirus, varicella zoster virus, JC virus and enterovirus, 3) panel for paraneoplastic antibodies, and rheumatologic/connective tissue disorders (antibodies to DNAdc, Sm, Rib-P, PCNA, U1-RNP, SS-A/Ro, SS-B/La, Sc1-70, CENP-B, RNA Pol III, Jo-1, Mi-2, PM-Scl, and ANCA), complement levels, 4) serum protein electrophoresis, 5) tumor markers: CEA, AFP, Ca 19.9, PSA, and B-2-microglobulina. The patient was found to have low levels of thyroid peroxidase antibodies (156 IU/ml) and thyroglobulin antibodies (158 IU/ml).

After excluding an infectious etiology, the patient was started on corticosteroids and IVIG without significant effect. One week later, he received 5 plasma exchange treatments without clinical effect and no change in the MRI (FIG. 2 D-F). By this time laboratory studies revealed serum and CSF antibodies against the cell surface of neurons, and he was started on cyclophosphamide (1 g per m$^2$/month) and rituximab (1 g every 2 weeks). Despite these treatments the patient showed no clinical or radiological improvement and continued with electrographic status epilepticus. Repeat MRIs showed new FLAIR/T2 abnormalities diffusely involving cortex (FIG. 2 G-I), and the patient died two months after admission.

c) Results

Six patients including the two index cases whose serum was used for immunoprecipitation and 4 additional cases whose serum was used for immunocompetition studies led to the initial characterization of GABA(A)R as the autoantigen of the disorder (described below). All 6 patients (5 male; age range, 3-63 years, median 22) with serum and CSF showing similar reactivity with the neuropil of rat brain (each blocking the reactivity of the others in immunocompetition studies) developed a rapidly progressive encephalopathy that eventually resulted in refractory seizures in all patients, and status epilepticus and/or epilepsia partialis continua in 5 (Table 1). In all patients the epileptic symptoms were preceded or associated with change of behavior or cognition; in addition some patients developed confusion, dyskinesias, psychiatric symptoms, verbal dysfunction, or focal motor deficits. One of the youngest patients (male 3 years old) had additional antibodies against the GABA(B)R; in addition to seizures, he also developed confusion, opsoclonus, ataxia and chorea. Five patients had abnormal CSF, including mild pleocytosis (median 75 WBC/microliter, range 23-154), increased protein concentration (median 60, range 59-60 mg/dL) and/or oligoclonal bands. All six patients had abnormal brain MRI, frequently showing extensive FLAIR/T2 abnormalities, with multifocal or diffuse cortical involvement without contrast enhancement (FIG. 1 and FIG. 2); one patient also had involvement of basal ganglia. In all patients the EEG showed epileptic activity; two of them with periodic generalized discharges (FIG. 3). In addition to GABA(A)R antibodies, 3 patients had thyroid peroxidase (TPO) antibodies, one glutamic acid decarboxylase 65 (GAD65) antibodies, and two GABA(B)R antibodies (see below). Other findings suggesting a propensity to autoimmunity or immune dysregulation included a past history of Hodgkin's lymphoma in one patient, and idiopathic thrombocytopenic purpura in another.

Treatment and follow-up were assessable in all 6 patients: 1 child received levetiracetam without immunotherapy and had substantial recovery (long-term follow-up not available). The other 5 received immunotherapy and multiple anti-epileptics, 4 of them requiring pharmacologic induced coma. Three of these patients had total or partial recovery, and 2 died as a result of sepsis during hospitalization for status epilepticus. One of them was the child with concomitant GABA(B)R antibodies indicated above (GABA(A)R antibodies were identified after his death in archived serum and CSF samples; clinical and pathological details previously described[18]). The oldest patient of the series (63 years) also had GABA(B)R antibodies; he fully recovered from the severe GABA(A) and GABA(B)-associated encephalopathy, and 7 years later developed diplopia and hemiataxia with GAD antibodies from which he also fully recovered.

In addition to the 6 patients with high serum and CSF titers of GABA(A)R antibodies, 12 patients had low titers of antibodies in serum. Three of these patients had negative CSF antibody studies and from the other 9 no CSF was available. In these 12 patients the presence of GABA(A)R antibodies could only be demonstrated with live CBA (HEK cells expressing alpha 1/beta 3 subunits of the GABA(A)R); no GABA(A)R-related reactivity was detected with sections of rat brain and only samples 7-13 showed mild reactivity with cultured neurons. Clinical information is shown in Table 3. In brief, all 6 patients with encephalitis had seizures, one of them (case #7; 2 year-old male) with refractory status epilepticus that required pharmacologic induced coma. Among the other 6 patients, 2 had opsoclonus-myoclonus, and 4 stiff-person syndrome.

Overall, 6 out of 12 patients had other neuronal antibodies in addition to GABA(A)R antibodies: 5 had GAD and 1 NMDAR antibodies. Additional findings suggesting a propensity to autoimmunity or immune dysregulation included, TPO antibodies in 1 patient, type 1 diabetes mellitus in 2, and Hashimoto's thyroiditis in 1.

Treatment and follow-up were assessable in 6 patients. Immunotherapy was used in 5/6 patients: 1 had full recovery, 3 partial recovery and 1 died. The patient who did not receive immunotherapy had stiff-person syndrome that was controlled symptomatically with clobazam and baclofen.

Example 2: Immunohistochemistry of Rat Brain

Adult female Wistar rats were sacrificed without perfusion, and the brain was removed and fixed by immersion in 4% paraformaldehyde for 1 hour at 4° C., cryoprotected in 40% sucrose for 48 hours, embedded in freezing compound media, and snap frozen in isopentane chilled with liquid nitrogen. Seven-micrometer-thick tissue sections were then sequentially incubated with 0.3% $H_2O_2$ for 15 minutes, 5% goat serum for 1 hour, and patient or control serum (1:200), CSF (1:5) at 4° C. overnight. After using the appropriate secondary biotinylated antibodies (goat anti-human BA-3000, dilution 1:2000), the reactivity was developed with the avidin-biotin-peroxidase method, as reported.[1]

Example 3: Immunocytochemistry on Neuronal Cultures

Rat hippocampal neuronal cultures were prepared as reported.[5] Live neurons grown on coverslips were incubated for 1 hour at 37° C. with patient or control serum (final dilution 1:200) or CSF (1:10). After removing the media and extensive washing with phosphate-buffered saline (PBS), neurons were fixed with 4% paraformaldehyde, permeabilized with 0.1% Triton X-100, and immunolabeled with Alexa Fluor 488 goat anti-human IgG (dilution 1:1000, Invitrogen, A11013). Results were photographed under a fluorescence microscope using Zeiss Axiovision software (Zeiss, Thornwood, N.Y.).

Example 4: Immunocytochemistry on HEK293 Cells a) Fixed Cells

HEK293 cells were transfected with plasmids containing the human alpha 1 subunit of the GABA(A)R (accession number: NM 000806.3; Origene catalog number: SC119668; SEQ ID NO.: 1) or the human beta 3 subunit of the receptor (accession number: NM 000814.3; Origene catalog number: SC125324; SEQ ID NO: 2); cells transfected with a plasmid without insert was used as control. Cells were grown for 24 hours after transfection before assessment. Transfected cells were fixed in 4% paraformaldehyde, permeabilized with 0.3% Triton X-100 and then incubated with patients' serum (1:20 and higher serial dilutions) or CSF (1:5 and higher serial dilutions) along with a commercial mouse antibody against the alpha 1 subunit of the GABA(A)R (dilution 1:5000, Millipore, MAB339) or beta 3 subunits (dilution 1:5000, Abcam AB4046) for 2 hours at room temperature, and the corresponding fluorescent secondary antibodies (Alexa Fluor 488 goat anti-human IgG, A11013, dilution 1:1000; and Alexa Fluor 594 goat anti-mouse IgG, A11032, dilution 1:1000; both from Invitrogen). Results were photographed under a fluorescence microscope using Zeiss Axiovision software.

b) Live Cells

Live HEK cells were incubated with serum (1:20 and higher serial dilutions) or CSF (1:5 and higher serial dilutions) of the patient together with the same commercial antibodies against GABA(A)R indicated above for 1 hour at 37° C., washed, fixed with 4% paraformaldehyde for 5 minutes. After washing cells were then incubated with the corresponding Alexa Fluor secondary antibodies indicated above.

Example 5: Immunoprecipitation and Immunoblot

Live neurons obtained as above, were grown in 100 mm plates (density 1.5×10$^6$ neurons/plate), and incubated at 37° C. with filtered patient serum (dilution 1:200) for 1 hour. Neurons were then washed with PBS, lysed with buffer (NaCl 150 mM, EDTA 1 mM, tris (hydroxymethyl) aminomethane [Tris]-HCl 100 mM, deoxycholate acid 0.5%, 1% Triton X-100, pH 7.5) containing protease inhibitors (P8340; Sigma Labs), and centrifuged at 16.1×10$^3$ g for 20 minutes at 4° C. The supernatant was retained and incubated with protein A/G agarose beads (20423; Pierce, Rockford, Ill.) overnight at 4° C., centrifuged, and the pellet containing the beads with patients' antibodies bound to the target cell surface antigen was then washed with lysis buffer, aliquoted, and kept at −80° C. An aliquot of this pellet was resuspended in Laemmli buffer, boiled for 5 minutes, separated in a 4 to 15% sodium dodecyl sulfate polyacrylamide gel electrophoresis, and the proteins visualized with EZBlue gel staining (G1041; Sigma Labs). Due to the lack of differences between the EZBlue-visible bands between patient's and control samples, all precipitated proteins run along the gel were analyzed using mass spectrometry.

Example 6: Mass Spectrometry

Mass spectrometry was performed at the Proteomics Facility at the Abramson Cancer Center of the University of Pennsylvania. Protein bands were trypsin digested and analyzed with a nano liquid chromatography (nano LC)/nanospray/linear ion trap (LTQ) mass spectrometer (Thermo Electron Corporation, San Jose, Calif.) as reported.[27] Briefly, 3 ml trypsin digested sample was injected with autosampler from Eksigent (Dublin, Calif.). The digested samples were separated on a 10 cm C18 column, using nano LC from Eksigent with 200 ml/minute flow rate, 45 minute gradient. Online nanospray was used to spray the separated peptides into LTQ, and Xcalibur software (Thermo Scientific, Waltham, Mass.) was utilized to acquire the raw data. The raw data files were searched using Mascot (Matrix Science, Boston, Mass.) against the NCBI and Swissprot databases (Swiss Institute of Bioinformatics (Basel, Switzerland).

Example 7: Immunoabsorption and Immunocompetition Studies

In order to determine whether the brain reactivity of patient's antibodies was specifically due to GABA(A)R binding, six 60 mm plates of HEK 293 cells expressing GABA(A) were sequentially incubated with patient's serum (1:200), each plate for 1 hour at 37° C. After incubation with the six plates, the immunoabsorbed serum was incubated with sections of rat hippocampus, as above. Patient's serum absorbed with non-transfected HEK 293 cells served as control.

To determine whether patients' antibodies were directed against similar antigens and epitopes of GABA(A)R, immunocompetition studies were performed. IgG was isolated from a patient whose serum contained high levels of IgG antibodies against GABA(A)R using protein A and G sepharose beads, and subsequently eluted and labeled with biotin, as reported (ref). Then, sections of rat brain were incubated with other patients' or control sera (diluted 1:5) overnight at 4° C., washed in PBS, and subsequently incubated with the indicated human biotinylated IgG containing GABA(A)R antibodies (dilution 1:40) for 1 hour at room temperature, and the reactivity was developed using the avidin-biotin-peroxidase method. Two sera were considered to compete for the same GABA(A)R epitopes, when pre-incubation of the tissue with one serum abrogated the reactivity of the other patient's IgG.

Example 8: Quantitative Analysis of Neuronal GABA(A)R Immunolabeling by Patient's Antibodies To determine the degree of immunolabeling of GABA (A)R by patient's antibodies, 14-day in vitro (div) rat hippocampal neurons were incubated with a representative patient's CSF (dilution 1:20) for 30 minutes, then washed, fixed, and incubated with a commercial mouse monoclonal antibody (Millipore 05-474; 1:500) against a sequence contained in the beta ⅔ subunit (which is a component of most GABA(A)R[30]) followed by appropriate fluorescent-conjugated secondary antibodies, Alexa Fluor 488 goat anti-human IgG (A11013; dilution 1:200) and Alexa Fluor 594 donkey anti-mouse IgG (A21203; dilution 1:200, both from Invitrogen). Images were obtained with a laser-scanning confocal microscope (Leica TCS SP5). Laser light levels and detector gain and offset were adjusted in every experiment so that no pixel values were saturated in any treatment conditions. Images were thresholded, and the number of individual clusters along neuronal dendrites was determined using interactive software (ImageJ).

Example 9: Analysis of the Structural Effects of Patient's Antibodies on GABA(A)R Clusters To determine the effects of patient's antibodies on the number and localization of GABA(A)R clusters, 14 div rat hippocampal neurons were treated with patient's or control CSF (1:20 dilution in Neuro-Basal+B27 medium; GIBCO, Carlsbad, Calif.) for 2 days. Every day, 20 of the 300 microliters medium in each culture well were removed and replaced with 20 microliters fresh patient or control CSF. On 16 div, neurons were fixed in freshly made paraformaldehyde (4% paraformaldehyde, 4% sucrose in phosphate-buffered saline) for 5 minutes, permeabilized in 0.25% Triton X-100 for 10 minutes, and blocked in 5% normal goat serum for 1 hour. Neurons were then incubated with the indicated monoclonal antibody against the GABA(A)R beta ⅔ (dilution 1:500), or a mouse monoclonal antibody against Gephyrin (dilution 1:200, Synaptic Systems, 147011), or a guinea pig polyclonal antibody against vesicular-GABA transporter (VGAT, dilution 1:1000; Synaptic Systems, 131004) or a rabbit antibody against GluN1 (anti-NMDAR1, dilution 1:100; Millipore, AB9864R) for 2 hours, followed by the appropriate fluorescent-conjugated secondary antibodies (Alexa Fluor 488 goat anti mouse IgG, A-11001, dilution 1:200; Alexa Fluor 594 goat anti-guinea pig IgG, A-11076, dilution 1:200; Cy5 donkey anti-rabbit IgG, dilution 1:200, Jackson ImmunoResearch 711-175-152). Images were obtained and analyzed as above.

Example 10: Identification of the Target Antigen as the GABA(A)R

Using rat brain immunohistochemistry the serum and CSF of the two index patients and 4 additional patients produced a similar pattern of neuropil reactivity (FIG. 4, A; FIG. 5). Subsequent studies with cultures of live rodent hippocampal neurons demonstrated that the target antigen was on the cell surface (FIG. 4, B). Immunoprecipitation of the target antigen using a patient's serum, followed by electrophoretic protein separation and EZBlue gel staining did not produce any specific band compared with the control serum (data not shown). Mass spectrometry of all separated proteins demonstrated that the patient's serum, but not the control serum, had precipitated protein fragments containing three sequences of the GABA(A)R (beta 3 subunit; Table 2).

Example 11: Patients' Antibodies Recognize a GABA(A)R Subunit Expressed on HEK Cells (Cell Based Assay)

Because the beta 3 subunits form complexes with the alpha 1 subunit of the GABA(A)R, we tested the reactivity of patients' antibodies with HEK cells transfected with the human alpha 1 or beta 3 subunits, or a combination of both. These experiments showed that all patients serum or CSF recognized the co-expression of alpha 1/beta 3 subunits, but when the subunits were individually assessed, four patients' samples recognized both the alpha 1 and beta 3 subunits, one only the alpha 1 subunit, and another required the co-expression of alpha 1/beta 3. For this reason the co-expression of both subunits was used for the determination of titers (Table 1). To optimize the CBA, we compared the sensitivity of the assay using live or fixed and permeabilized HEK cells (live-CBA, or fixed-CBA) expressing the alpha 1/beta 3 subunits of the GABA(A)R. These studies showed that all patients CSF antibodies were detectable with live or fixed CBA, but serum antibodies were predominantly visible with live CBA (FIG. 6).

Immunoabsorption of a representative serum (that competed with the other 5 patients' antibodies for the same brain epitopes) with HEK cells expressing the alpha 1/beta 3 subunits of the GABA(A)R resulted in abrogation of reactivity with rat brain and cultures of neurons, further confirming that this reactivity was with the GABA(A)R (FIG. 7).

Example 12: Identification of Two Immunological Groups of Patients

Using the indicated live CBA, 12 additional patients with antibodies against the GABA(A)R subunit were identified. In these 12 patients the serum antibody titer using serial dilutions of samples was always <1:160; from 3 of these patients (cases #7, 12 and 18) the CSF was available and all were negative; from the other 9 patients no CSF was available. A summary of these patients is discussed herein above and shown in table 3. In brief, 5 patients had encephalitis with prominent seizures (one with refractory status epilepticus required pharmacologically-induced coma), 1 had anti-NMDAR encephalitis, 2 opsoclonus-myoclonus, and 4 stiff-person syndrome (2 of them in association with GAD antibodies).

Overall, these experiments revealed two immunological groups of patients, (1) the 6 patients described above with high titers of antibodies in serum (>1:160) and CSF, and (2) the 12 patients with low titers of antibodies in serum and/or absent antibodies in CSF. While the antibodies in patients of the first group were demonstrated with three techniques (immunohistochemistry with rat brain, cultured neurons, and CBA), the antibodies in patients of the second group were only detectable with live CBA (all cases) and cultured live neurons (cases #7-13).

Example 13: Patient's Antibodies Selectively Bind to Neuronal GABA(A)R and Remove the Receptors from Synapses The following studies were performed with CSF of a representative patient which brain reactivity was specific for only GABA(A)R antibodies. The reactivity was abrogated by pre-absorption with HEK cells expressing GABA(A)R (similar as FIG. 7), and by immunocompetition assays with antibodies from the other 5 patients with high titer antibodies, indicating that all patients' antibodies targeted the same epitopes (FIG. 8). To examine the extent of recognition of GABA(A)R by patient's CSF antibodies, the GABA(A)R immunolabeling was quantified by confocal microscopy (FIG. 9A). These results suggest that 89% of patient's antibodies labeled GABA(A)R-containing clusters (FIG. 9B). In order to examine the effects of patient's antibodies on inhibitory synapses containing GABA(A)R, neurons were treated with patient's CSF antibodies or a control CSF for 48 hours. These studies showed that the density of GABA(A)R clusters along dendrites was not significantly decreased (FIG. 9 C, left panel, green puncta, FIG. 9D), but the clusters of GABA(A)R in synapses, measured as puncta density co-labeled by the presynaptic marker vGAT were greatly reduced (FIG. 9 C, right panel yellow puncta as overlay between green and red puncta, FIG. 9E). This finding suggests that antibodies present in patient's CSF, but not control CSF, removed. GABA(A)R from synaptic sites. The effect was specific to GABA(A)R since the cluster density of other synaptic markers such as gephyrin (FIG. 9 F) and the GluN1 subunit of the NMDAR (data not shown) were not affected.

REFERENCE LIST

1. Ances B M, Vitaliani R, Taylor R A, Liebeskind D S, Voloschin A, Houghton D J, Galetta S L, Dichter M, Alavi A, Rosenfeld M R, Dalmau J. Treatment-responsive limbic encephalitis identified by neuropil antibodies: MRI and PET correlates. Brain 2005; 128:1764-1777.
2. Andrade D M, Tai P, Dalmau J, Wennberg R. Tonic seizures: a diagnostic clue of anti-LGI1 encephalitis? Neurology 2011; 76:1355-1357.
3. Bayreuther C, Bourg V, Dellamonica J, Borg M, Bernardin G, Thomas P. Complex partial status epilepticus revealing anti-NMDA receptor encephalitis. Epileptic Disord 2009; 11:261-265.
4. Blanc F, Ruppert E, Kleitz C, Valenti M P, Cretin B, Humbel R L, Honnorat J, Namer I J, Hirsch E, Manning L, de Seze J. Acute limbic encephalitis and glutamic acid decarboxylase antibodies: a reality? J Neural Sci 2009; 287:69-71.
5. Buchhalter J R, Dichter M A. Electrophysiological comparison of pyramidal and stellate nonpyramidal neurons in dissociated cell culture of rat hippocampus. Brain Res Bull 1991; 26:333-338.
6. Dalmau J. Status epilepticus due to paraneoplastic and nonparaneoplastic encephalitides. Epilepsia 2009; 50 Suppl 12:58-60.
7. Dalmau J, Gleichman A J, Hughes E G, Rossi J E, Peng X, Lai M, Dessain S K, Rosenfeld M R, Balice-Gordon R, Lynch D R. Anti-NMDA-receptor encephalitis: case series and analysis of the effects of antibodies. Lancet Neurol 2008; 7:1091-1098.
8. Florance N R, Davis R L, Lam C, Szperka C, Zhou L, Ahmad S, Campen C J, Moss H, Peter N, Gleichman A J, Glaser C A, Lynch D R, Rosenfeld M R, Dalmau J. Anti-N-methyl-D-aspartate receptor (NMDAR) encephalitis in children and adolescents. Ann Neurol 2009; 66:11-18.
9. Glaser C A, Honarmand S, Anderson L J, Schnurr D P, Forghani B, Cossen C K, Schuster F L, Christie L J, Tureen J H. Beyond viruses: clinical profiles and etiologies associated with encephalitis. Clin Infect Dis 2006; 43:1565-1577.
10. Gonzalez M I. The possible role of GABAA receptors and gephyrin in epileptogenesis. Front Cell Neurosci 2013; 7:113.
11. Höftberger, R., Titulaer, M. J., Sabater, L., et al. Encephalitis and GABA(B) Receptor Antibodies: Novel Findings in a New Case Series of 20 Patients. Neurology. 2013.
12. Honnorat J, Saiz A, Giometto B, Vincent A, Brieva L, de Andres C, Maestre J, Fabien N, Vighetto A, Casamitjana R, Thivolet C, Tavolato B, Antoine J, Trouillas P, Graus F. Cerebellar ataxia with anti-glutamic acid decarboxylase antibodies: study of 14 patients. Arch Neurol 2001; 58:225-230.
13. Hughes E G, Peng X, Gleichman A J, Lai M, Zhou L, Tsou R, Parsons T D, Lynch D R, Dalmau J, Balice-Gordon R I Cellular and synaptic mechanisms of anti-NMDA receptor encephalitis. J Neurosci 2010; 30:5866-5875.
14. Irani S R, Alexander S, Waters P, Kleopa K A, Pettingill P, Zuliani L, Peles E, Buckley C, Lang B, Vincent A. Antibodies to Kv1 potassium channel-complex proteins leucine-rich, glioma inactivated 1 protein and contactin-associated protein-2 in limbic encephalitis, Morvan's syndrome and acquired neuromyotonia. Brain 2010; 133: 2734-2748.
15. Irani S R, Michell A W, Lang B, Pettingill P, Waters P, Johnson M R, Schott J M, Armstrong R J, Zagami S, Bleasel A, Somerville E R, Smith S M, Vincent A. Faciobrachial dystonic seizures precede Lgi1 antibody limbic encephalitis. Ann Neurol 2011; 69:892-900.
16. Jeffery O J, Lennon V A, Pittock S J, Gregory J K, Britton J W, McKeon A. GABAB receptor autoantibody frequency in service serologic evaluation. Neurology 2013; 81:882-887.
17. Johnson N, Henry C, Fessler A J, Dalmau J. Anti-NMDA receptor encephalitis causing prolonged nonconvulsive status epilepticus. Neurology 2010; 75:1480-1482.
18. Kruer, M. C., Lim, K. Y., Hoftberger, R., Svoboda, M. D., Woltjer, R. L., Dalmau, J. Opsoclonus, Ataxia, Chorea, and Seizures in Pediatric GABA(B) Receptor Autoimmunity. JAMA Neurol. 2013.
19. Lai M, Hughes E G, Peng X, Zhou L, Gleichman A J, Shu H, Mata S, Kremens D, Vitaliani R, Geschwind M D, Bataller L, Kalb R G, Davis R, Graus F, Lynch D R, Balice-Gordon R, Dalmau. J. AMPA receptor antibodies in limbic encephalitis alter synaptic receptor location. Ann Neurol 2009; 65:424-434.
20. Lai M, Huijbers M G, Lancaster E, Graus F, Bataller L, Balice-Gordon R, Cowell J K, Dalmau J. Investigation of LGI1 as the antigen in limbic encephalitis previously attributed to potassium channels: a case series. Lancet Neurol 2010; 9:776-785.
21. Lancaster E, Dalmau. J. Neuronal autoantigens-pathogenesis, associated disorders and antibody testing. Nat Rev Neurol 2012; 8:380-390.
22. Lancaster E, Lai M, Peng X, Hughes E, Constantinescu. R, Raizer J, Friedman D, Skeen M B, Grisold W, Kimura A, Ohta K, Iizuka T, Guzman M, Graus F, Moss S J, Balice-Gordon R, Dalmau J. Antibodies to the GABA(B) receptor in limbic encephalitis with seizures: case series and characterisation of the antigen. Lancet Neurol 2010; 9:67-76.
23. Lancaster E, Martinez-Hernandez E, Dalmau J. Encephalitis and antibodies to synaptic and neuronal cell surface proteins. Neurology 2011; 77:179-189.
24. Malter M P, Helmstaedter C, Urbach H, Vincent A, Bien C G. Antibodies to glutamic acid decarboxylase define a form of limbic encephalitis. Ann Neurol 2010; 67:470-478.
25. Mukherjee J, Kretschmannova K, Gouzer G, Maric H M, Ramsden S, Tretter V, Harvey K, Davies P A, Trifler A, Schindelin H, Moss S J. The residence time of GABA (A)Rs at inhibitory synapses is determined by direct binding of the receptor alpha1 subunit to gephyrin. J Neurosci 2011; 31:14677-14687.
26. Saiz A, Blanco Y, Sabater L, Gonzalez F, Bataller L, Casamitjana R, Ramio-Torrenta L, Graus F. Spectrum of neurological syndromes associated with glutamic acid decarboxylase antibodies: diagnostic clues for this association. Brain 2008; 131:2553-2563.
27. Strader M B, Tabb D L, Hervey W J, Pan C, Hurst G B. Efficient and specific trypsin digestion of microgram to nanogram quantities of proteins in organic-aqueous solvent systems. Anal Chem 2006; 78:125-134.

28. Titulaer M J, McCracken L, Gabilondo I, Armangue T, Glaser C, Iizuka T, Honig L S, Benseler S M, Kawachi I, Martinez-Hernandez E, Aguilar E, Gresa-Arribas N, Ryan-Florance N, Torrents A, Saiz A, Rosenfeld M R, Balice-Gordon R, Graus F, Dalmau J. Treatment and prognostic factors for long-term outcome in patients with anti-NMDA receptor encephalitis: an observational cohort study. Lancet Neurol 2013; 12:157-165.

29. Tretter V, Moss S J. GABA(A) Receptor Dynamics and Constructing GABAergic Synapses. Front Mol Neurosci 2008; 1:7.

30. Vithlani M, Terunuma M, Moss S J. The dynamic modulation of GABA(A) receptor trafficking and its role in regulating the plasticity of inhibitory synapses. Physiol Rev 2011; 91:1009-1022.

31. Zhou C, Huang Z, Ding L, Deel M E, Arain F M, Murray C R, Patel R S, Flanagan C D, Gallagher M I Altered cortical GABAA receptor composition, physiology, and endocytosis in a mouse model of a human genetic absence epilepsy syndrome. J Biol Chem 2013; 288:21458-21472.

32. Gable M S, Sheriff H, Dalmau J, Tilley D H, Glaser C A. The Frequency of Autoimmune N-Methyl-D-Aspartate Receptor Encephalitis Surpasses That of Individual Viral Etiologies in Young Individuals Enrolled in the California Encephalitis Project. Clin Infect Dis 2012.

33. Gable M S, Gavali S, Radner A, Tilley D H, Lee B, Dyner L, et al. Anti-NMDA receptor encephalitis: report of ten cases and comparison with viral encephalitis. *Eur J Clin Microbiol Infect Dis* 2009; 28:1421-1429.

34. Raoult, D., and Dasch, G. A. (1989), The line blot: an immunoassay for monoclonal and other antibodies. Its application to the serotyping of gram-negative bacteria. J. Immunol. Methods, 125 (1-2), 57-65.

35. WO2013041540

36. U.S. Pat. No. 4,647,543

37. Voigt, J., Krause, C., Rohwäder, E, Saschenbrecker, S., Hahn, M., Danckwardt, M., Feirer, C., Ens, K, Fechner, K, Barth, E, Martinetz, T., and Stocker, W. (2012), Automated Indirect Immunofluorescence Evaluation of Antinuclear Autoantibodies on HEp-2 Cells," Clinical and Developmental Immunology, vol. 2012, doi:10.1155/2012/651058.

38. Bonilla, E., Francis, L., Allam, F. et al., "Immunofluorescence microscopy is superior to fluorescent beads for detection of antinuclear antibody reactivity in systemic lupus erythematosus patients," Clinical Immunology, vol. 124, no. 1, pp. 18-21, 2007.

39. Ronspeck W, Brinckmann R, Egner R, Gebauer F, Winkler D, Jekow P, et. al. Peptide based adsorbers for therapeutic immunoadsorption. Ther Apher Dial 2003 February; 7(1):91-7.

TABLE 1

Clinical features of patients with GABA(A)R antibodies

| # | Sex age | Main Symptoms | Other | CSF | MRI | EEG | Treatment | Outcome | Subunit target alpha 1/beta 3 titers |
|---|---|---|---|---|---|---|---|---|---|
| 1 | F, 16 | Several months of memory problems, cognitive dysfunction, worsening social anxiety, depressed mood and fatigue. Four days before admission developed headache, fatigue, vertigo, nausea, and scintillating scotomas. Five days after admission developed tonic-clonic seizures that rapidly progressed to frequent seizures and status epilepticus | Hodgkin's lymphoma treated with chemotherapy and radiotherapy. At presentation she had been cancer free for 10 months. Brain biopsy on day 14 showed intense diffuse reactive astrocytic gliosis, microglial activation, and a population of reactive T lymphocytes | 23 WBC/μL (69% lymphocytes); protein 60 mg/dL; Repeat study after 5 months: normal | Multiple foci of high T2/FLAIR signal in both hemispheres, without diffusion restriction. Repeat study at 5 months: Numerous new multifocal lesions and diffuse cortical atrophy. Repeat study at 6 months: no new lesions, improvement or resolution of all previous lesions and reduction of diffuse atrophy | Initial EEG generalized slowing with bitemporal epileptiform activity. Late in the first month of admission generalized periodic epileptiform discharges | Anticonvulsants: Levetiracetam, topiramate, midazolam, phenobarbital coma for 4 months Immunosuppressants: High-dose methylprednisolone, IVIG, plasma exchange, rituximab, cyclophosphamide, mycophenolate mofetil | Three months after admission, progressive neurological recovery with gradual resolution of the EEG pattern. Six months after admission more rapid neurological recovery. Discharged to rehabilitation at 7 months, and home at 10 months; able to walk with limited assistance, communicate, and perform most daily activities independently. She continues to have improvements in cognitive function and short term memory. | Serum: alpha 1, beta 3 alpha 1/beta 3 (>1/1280) CSF: alpha 1 alpha 1/beta 3 (>1/320) |
| 2 | M, 51 | Behavioral changes, initially with depressive features progressing to psychotic symptoms and mutism. Generalized pruritus. Several weeks after presentation developed epilepsia partialis continua and | Ischemic stroke of right middle cerebral artery at age 46 (multiple cardio-vascular risk factors), idiopathic thrombocytopenic purpura (splenectomy) Low titers of TPO | Normal WBC and protein concentration; OB positive | Multifocal T2/FLAIR hyperintensities with generalized cortical involvement | Temporal epileptiform activity with secondary generalization. Repeat studies showed periodic generalized discharges | Anticonvulsants: Levetiracetam, diazepam, lacosamide, phenytoin, midazolam, propofol, thiopental Immunosuppressants: Steroids, IVIG, plasma exchange, cyclophosphamide and rituximab | Status epilepticus persisted for more than 10 weeks, when the patient died of sepsis | Serum: alpha 1, beta 3 alpha 1/beta 3 (>1/1280) CSF: alpha 1 alpha 1/beta 3 (>1/320) |

TABLE 1-continued

Clinical features of patients with GABA(A)R antibodies

| # | Sex age | Main Symptoms | Other | CSF | MRI | EEG | Treatment | Outcome | Subunit target alpha 1/beta 3 titers |
|---|---|---|---|---|---|---|---|---|---|
| 3 | M, 28 | status epilepticus Behavioral and cognitive changes, complex partial seizures, status epilepticus | and Tg antibodies Positive TPO antibodies | <5 WBC/μL; protein <45 mg/dL | Persistent bilateral mesiotemporal hyperintensity on FLAIR | Epileptiform activity, pharmacological induced burst suppression | Anticonvulsants Propofol, midazolam, levetiracetam, phenytoin, phenobarbital, topiramate, clobazam, thiopental Immunosuppressants: IV corticosteroids then oral taper | 8 week ICU admission. Discharged to rehabilitation center for management of critical illness myopathy and cognitive impairment and gradually returned to baseline function. At last follow-up, 18 months from presentation the patient was well, seizure free, on no medications, and had returned to his previous employment. | Serum: alpha 1, beta 3 alpha 1/beta 3 (>1/640) CSF: alpha 1, beta 3 alpha 1/beta 3 (>1/160) |
| 4 | M, 3 | Confusion, lethargy, opsoclonus, dystonic tongue movements, ataxia and chorea affecting limbs and trunk. Within 24 hours developed frequent complex partial seizures and status epilepticus | Positive GABA(B)R antibodies in serum and CSF Cerebellar biopsy demonstrated widespread astrogliosis and microglial activation with Purkinje and granule cell loss | 154 WBC/μL (94% L); 228 RBC/μL; protein 59 mg/dL | Multifocal DWI hyperintensities within the brainstem and cerebellum without corresponding ADC restriction. Repeat study: evolution of lesions to T2/FLAIR hyperintensity with involvement of the basal ganglia and hippocampi | Diffuse delta range slowing and bilateral occipital spike-wave discharges with rapid secondary generalization into poly-spike and slow wave discharges followed by attenuation | Anticonvulsants: Multiple. Pentobarbital induced coma. Due to worsening cerebral edema, a decompressive posterior craniectomy was performed. Immunosuppressants: High-dose intravenous corticosteroids and IVIG without clear benefit. | Electrographic seizures persisted despite administration of multiple anticonvulsants and were eventually controlled with continuous infusion of pentobarbital. Status epilepticus recurred when weaning was attempted. Despite intensive supportive care and aggressive seizure management, 4 weeks after the initial presentation the patient developed overwhelming sepsis and died. No autopsy was performed. | Serum: n/a CSF: alpha 1, beta 3 alpha 1/beta 3 (>1/320) |

TABLE 1-continued

Clinical features of patients with GABA(A)R antibodies

| # | Sex age | Main Symptoms | Other | CSF | MRI | EEG | Treatment | Outcome | Subunit target alpha 1/beta 3 titers |
|---|---|---|---|---|---|---|---|---|---|
| 5 | M, 4 | Progressive right hemiparesis followed 2 months later with partial complex seizures that evolved to status epilepticus | | Increased WBC and protein concentration | Abnormal FLAIR MRI changes suggesting encephalitis | Initially generalized slowing. Repeat study showed slow activity with epileptiform discharges | Anticonvulsants: Levetiracetam Immunosuppresssants: No | Status epilepticus was controlled with anticonvulsants and seizures did not recur during admission. | Serum: alpha 1 alpha 1/beta 3 (>1/320) CSF: negative with alpha 1 and beta 3 expressed alone alpha 1/beta 3 (>1/40) |
| 6 | M, 63 | Subacute onset of short term memory loss, gustatory and olfactory hallucinations, facial cramps, progressive deterioration with increasing psychomotor agitation, tinnitus | Type 2 Diabetes mellitus, hypertension Hypothyroidism Positive GABA(B)R, GAD, TPO and Tg antibodies | 75 WBC/μL; increased protein concentration; OB positive Repeat studies at relapse 7 years later: <5 WBC/μL; protein <45 mg/dL; OB positive | T2/FLAIR increased signal in the right temporal cortex without gadolinium enhancement or diffusion restriction | Epileptic activity in frontotemporal regions | Anticonvulsants: Valproate, levetiracetam, barbiturate Immunosuppresssants: Oral corticosteroids | After being symptom free for 7 years, he developed diplopia and hemiataxia without opsoclonus which spontaneously resolved. During the relapse GABA(A)R and GABA(B)R antibodies were not found but GAD antibodies persisted. | Serum: n/a CSF: negative with alpha 1 and beta 3 expressed alone alpha 1/beta 3 (>1/20) |

*CSF = cerebrospinal fluid, EEG = electroencephalography, F = female, FLAIR = fluid attenuated inversion recovery, GABA = gamma-aminobutyric acid, GAD = glutamic acid decarboxylase 65, IVIG = intravenous immunoglobulin, M = male, MRI = magnetic resonance imaging, NA = not available, NMDA = N-methyl-D-aspartate, OB = oligoclonal bands, Tg = thyroglobulin, TPO = thyroid peroxidase, WBC = white blood cells count, DWI = diffusion weighted imaging, ADC = apparent diffusion coefficient

TABLE 2

| Sequences isolated by immunoprecipitation with patient's serum | | | |
|---|---|---|---|
| Sequence | SEQ ID NO | Beta 3 subunit of the GABA(A)R, peptide identification probability | Sequest XCorr | Sequest deltaCn |
| (R)LHPDGTVLYGLR(I) (+3H) | SEQ ID NO: 7 | 95% | 2.97 | 0.21 |
| R)NVVFATGAYPR(L) (+2H) | SEQ ID NO: 8 | 95% | 3.21 | 0.55 |
| (R)VADqLWVPDTYFLnDKK(S) (+3H) | SEQ ID NO: 9 | 95% | 2.98 | 0.42 |

Mass spectral data was analyzed using the search engine Sequest. Peptide confidence was determined by the cross-correlation scoring which represent sensitivity, comparing the experimental fragmentation spectrum of the peptides against the theoretical predicted fragmentation spectrum; and by the DeltaCn, which represents specificity for the peptide identification. Xcorr>2 (+2H), 2.5 (+3H) and deltaCn>0.2) indicate a good spectrum.

TABLE 3

Main clinical features of 12 patients with low titer of GABA(A)R antibodies in serum and/or no antibodies in CSF

| # | Sex, age | Main Symptoms | Other | Initial CSF | MRI | EEG | Treatment | Outcome | Subunit target alpha 1/beta 3 titers |
|---|---|---|---|---|---|---|---|---|---|
| 7 | M, 2 year and 9 month (12-218) | Subacute onset of partial seizures, 4 month later developed refractory status epilepticus, neurological deterioration and abnormal choreathetotic movements | Muscle biopsy and extensive metabolic studies: Normal | Normal WBC and protein concentration | First MRI normal, repeat studies showed cortical atrophy attributed to steroids | Epileptic activity with right parietal predominance, generalized slowing. Burst suppression during pentobarbital induced coma. | Anticonvulsants: Carbamazepine, valproate, midazolam, levetiracetam, phenobarbital, pentobarbital induced coma Immunosuppressants: High-dose intravenous corticosteroids and oral taper Other: ketogenic diet, thiamine, riboflavine, clonidine, biperiden | Partial response with ketogenic diet and corticosteroids, slow progressive impairment of cognitive and motor skills. Partial seizures persisted at 18 month of follow up | Serum: beta 3 alpha 1/beta 3: 1/160) CSF: negative |
| 8 | M, 41 (08-758) | Subacute onset of secondary generalized seizures and fever. Progressive development of epilepsia partialis continua and aphasia. After 2 years developed several episodes of status epilepticus | GAD antibodies. | Normal WBC and protein concentration OB negative | First: mild increased signal in T2/FLAIR in left frontal lobe. Repeat study: multiple lesions in cortex and white matter in left frontal, temporal and occipital lobes Repeat study after 7 months normal and remains normal after 2 years | Epileptic abnormalities in bilateral (left>right) frontal areas | Anticonvulsants: Valproate, oxcarbamazepine, levetiractam Immunosuppressants: High-dose intravenous corticosteroids, low dose oral steroid long term treatment | Partial response to high-dose intravenous corticosteroids. Two years after presentation developed status epilepticus with good response to anticonvulsants adjustment and high-dose intravenous corticosteroids; GABA(A)R and GAD antibodies were negative | Serum: alpha1 alpha 1/beta 3: 1/160) CSF: n/a |
| 9 | F, 15 (10-494) | Diminished verbal output, seizures. | GAD antibodies | 8 WBC/μL; protein 34 mg/dL | Bilateral frontotemporal, right parietal and left frontal foci of increased T2/FLAIR signal with leptomeningeal enhancement | Multifocal epileptiform activity | NA | NA | Serum: alpha 1, beta 3 alpha 1/beta 3: 1/160) CSF: n/a |

TABLE 3-continued

Main clinical features of 12 patients with low titer of GABA(A)R antibodies in serum and/or no antibodies in CSF

| # | Sex, age | Main Symptoms | Other | Initial CSF | MRI | EEG | Treatment | Outcome | Subunit target alpha 1/beta 3 titers |
|---|---|---|---|---|---|---|---|---|---|
| 10 | F, 32 (10-530) | Multifocal refractory seizures. | Type 1 diabetes mellitus, Hashimoto's thyroiditis GAD, TPO and Tg antibodies | Normal WBC and protein concentration | Initial and subsequent MRI studies normal. | Multifocal epileptic waves, independent bilateral temporal lobe seizures | Anticonvulsants: Oxcarbazepine, carbamazepine, lacosamide, levetiracetam, zonisamide, topiramate, clobazam, phenytoin, lamotrigine Immunosuppressants: IVIG, Omalizumab corticosteroids, cyclosporine, hydroxychloroquine | Seven years after onset still has uncontrolled seizures (treated with phenytoin and lamotrigine), severe gastrointestinal dysmotility. Urticaria resolved. | Serum: negative with alpha 1 and beta 3 expressed alone (alpha 1/beta 3: 1/40) CSF: n/a |
| 11 | F, 74 (06-178) | Subacute onset of lethargy and alternating changes in level of consciousness, suspected temporal lobe seizures | Previous history of ovarian cancer | Normal WBC and protein concentration | Normal, repeat study also normal | Normal (at the time the patient was alert) | NA | NA | Serum: negative with alpha 1 and beta 3 expressed alone alpha 1/beta 3: 1/40) CSF: n/a |
| 12 | F, 16 (12-518) | Insomnia, progressive behavior abnormalities, decreased level of consciousness, orofacial dyskinesia, brief seizures | Positive serum and CSF NMDAR antibodies | 17 WBC/μL protein 24 mg/dL | First MRI normal, repeat study 2 month later showed increased signal intensity (cortical FLAIR, subcortical T1 in left superior temporal gyrus | Moderate to severe nonspecific diffuse slowing | Anticonvulsants: Valproate Immunosuppressants: High-dose intravenous corticosteroids, IVIG, plasmapheresis, rituximab | Seizure free after valproate. No clear benefit to first line immunosuppressive drugs. Three months after rituximab was initiated, dysautonomia, dyskinesia, and seizures resolved. Gradual improvement of neuropsychiatric/behavioral and language abnormalities over many months. | Serum: negative with alpha 1 and beta 3 expressed alone alpha 1/beta 3: 1/20) CSF: negative |
| 13 | M, 19 (02-699) | GAD-associated stiff-person syndrome | Type 1 diabetes mellitus, GAD antibodies | No lumbar puncture performed | Normal | Not done | Anticonvulsants: Clonazepam Immunosuppressants: No Other: baclofen | Stable, independent for daily activities | Serum: negative with alpha 1 and beta 3 expressed alone alpha 1/beta 3: 1/40 CSF n/a |
| 14 | M, 12 (10-260) | GAD-associated stiff-person syndrome (7 years of symptoms) | GAD antibodies | NA | NA | NA | NA | NA | Serum: negative with alpha 1 and beta 3 expressed alone alpha 1/beta 3:1/20) CSF n/a |
| 15 | M, 21 (02- | Stiff-person syndrome | Antinuclear antibodies | NA | NA | NA | NA | NA | Serum: negative with alpha 1 and |

TABLE 3-continued

Main clinical features of 12 patients with low titer of GABA(A)R antibodies in serum and/or no antibodies in CSF

| # | Sex, age | Main Symptoms | Other | Initial CSF | MRI | EEG | Treatment | Outcome | Subunit target alpha 1/beta 3 titers |
|---|---|---|---|---|---|---|---|---|---|
| | 527) | (5 years of symptoms) | 1/640 | | | | | | beta 3 expressed alone alpha 1/beta 3: 1/20) CSF n/a |
| 16 | M, ? (00-125) | Stiff-person syndrome | | NA | NA | NA | NA | NA | Serum: negative with alpha 1 and beta 3 expressed alone alpha 1/beta 3: 1/20) CSF n/a |
| 17 | F, 34 (00-151) | Opsoclonus-myoclonus syndrome | Idiopathic what? | NA | Normal | Not done | NA | NA | Serum: negative with alpha 1 and beta 3 expressed alone alpha 1/beta 3: 1/40) CSF n/a |
| 18 | M, 65 (94-131) | Opsoclonus myoclonus syndrome | Heavy smoker, ANA positive, Negative screening for neoplasia | Normal WBC and protein concentration | Normal | Not done | Immunosuppressants: Corticosteroids | No response, died a few months after onset | Serum: beta 3 alpha 1/beta 3 (1/20) CSF negative |

** All 12 patients had low titer (=<1/160) of GABA(A)R antibodies in serum; from patients #7, 12, and 18 CSF was available and was found negative for GABA(A)R antibodies; from the other 9 patients CSF was not available.

CSF = cerebrospinal fluid,
EEG = electroencephalography,
F = female,
FLAIR = fluid attenuated inversion recovery,
GABA = gamma-aminobutyric acid,
GAD = glutamic acid decarboxylase 65,
IVIG = intravenous immunoglobulin,
M = male,
MRI = magnetic resonance imaging,
NA = not available,
NMDA = N-methyl-D-aspartate,
OB = oligoclonal bands,
Tg = thyroglobulin,
TPO = thyroid peroxidase,
WBC = white blood cells count

The invention claimed is:

1. A method for prognosticating or diagnosing an autoimmune disease, the method comprising:
   a) bringing a liquid sample isolated from a subject suspected of comprising an autoantibody into contact with
      (i) a human or rat gamma-aminobutyric acid-A receptor (GABA(A)R) alpha 1 subunit linked to a reporter-molecule or to a solid phase,
      (ii) a human or rat GABA(A)R beta 3 subunit linked to a reporter-molecule or to a solid phase,
      (iii) a GABA(A)R having the sequence of SEQ ID NO: 1 or 2 linked to a reporter-molecule or to a solid phase, or
      (iv) a cell linked to a reporter-molecule or to a solid phase and expressing the human or rat GABA(A)R alpha 1 subunit, the human or rat GABA(A)R beta 3 subunit, or the GABA(A)R having the sequence of SEQ ID NO: 1 or 2,
   b) detecting the presence of the binding of the autoantibody to
      (i) the human or rat GABA(A)R alpha 1 subunit linked to a reporter-molecule or to a solid phase,
      (ii) the human or rat GABA(A)R beta 3 subunit linked to a reporter-molecule or to a solid phase,
      (iii) the GABA(A)R having the sequence of SEQ ID NOs: 1 or 2 or the variant of SEQ ID NO: 2 linked to a reporter-molecule or to a solid phase, or
      (iv) the cell linked to a reporter-molecule or to a solid phase,
   c) subsequent to detecting the presence of the binding, taking blood from the subject,
   d) contacting the blood with
      a pharmaceutical composition comprising
         (i) the human or rat GABA(A)R alpha 1 subunit,
         (ii) the human or rat GABA(A)R beta 3 subunit,
         (iii) the GABA(A)R having the sequence of SEQ ID NO: 1 or 2, or
         (iv) the cell expressing the human or rat GABA(A)R alpha 1 subunit, the human or rat GABA(A)R beta 3 subunit, or the GABA(A)R having the sequence of SEQ ID NO: 1 or 2, or
      a medical device coated with at least one of
         (i) the human or rat GABA(A)R alpha 1 subunit,
         (ii) the human or rat GABA(A)R beta 3 subunit,
         (iii) the GABA(A)R having the sequence of SEQ ID NO: 1 or 2, or
         (iv) the cell expressing the human or rat GABA(A)R alpha 1 subunit, the human or rat GABA(A)R beta 3 subunit, or the GABA(A)R having the sequence of SEQ ID NO: 1 or 2, and
   e) readministering the contacted blood from step d) to the subject,
   wherein said autoimmune disease is at least one disease selected from the group consisting of seizure, encephalitis and a combination thereof, and
   said liquid sample is at least one liquid sample selected from the group consisting of serum and cerebrospinal fluid (CSF).

2. The method of claim 1, wherein step b) is carried out using a method selected from the group consisting of immunofluorescence microscopy or spectroscopy, NMR spectroscopy, mass spectrometry, radioactivity, chemical crosslinking, surface plasmon resonance, native gel electrophoresis, chromatography or enzymatic activity.

3. The method of claim 1, wherein said liquid sample is brought into contact with said cell linked to a reporter-molecule or to a solid phase and expressing the human or rat GABA(A)R alpha 1 subunit, the human or rat GABA(A)R beta 3 subunit, or the GABA(A)R having the sequence of SEQ ID NO: 1 or 2.

4. The method of claim 1, wherein said autoimmune disease is selected from the group consisting of (i) encephalitis and seizure and (ii) seizure.

5. The method of claim 1, wherein said liquid sample is brought into contact with a combination of the human or rat GABA(A)R alpha 1 subunit linked to a reporter-molecule or to a solid phase and the human or rat GABA(A)R beta 3 subunit linked to a reporter-molecule or to a solid phase.

6. The method of claim 1, wherein said human or rat GABA(A)R alpha 1 subunit linked to a reporter-molecule or to a solid phase is according to SEQ ID NO:1 and said human or rat GABA(A)R beta 3 subunit linked to a reporter-molecule or to a solid phase is according to SEQ ID NO:2.

7. A method comprising:
   obtaining at least one liquid sample from a subject having an autoimmune disease, wherein the at least one liquid sample is selected from the group consisting of serum and cerebrospinal fluid (CSF);
   contacting the at least one liquid sample from the subject with
      (i) a human or rat gamma-aminobutyric acid-A receptor (GABA(A)R) alpha 1 subunit linked to a reporter-molecule or to a solid phase, (ii) a human or rat GABA(A)R beta 3 subunit linked to a reporter-molecule or to a solid phase,
(iii) a GABA(A)R having the sequence of SEQ ID NO: 1 or 2 linked to a reporter-molecule or a solid phase, or
(iv) a cell linked to a reporter-molecule or to a solid phase and expressing the human or rat GABA(A)R alpha 1 subunit, the human or rat GABA(A)R beta 3 subunit, or the GABA(A)R having the sequence of SEQ ID NO: 1 or 2, and subsequently, when the at least one liquid sample is cerebrospinal fluid (CSF), detecting the presence of the binding of an autoantibody to
  (i) the human or rat GABA(A)R alpha 1 subunit linked to a reporter-molecule or to a solid phase,
  (ii) the human or rat GABA(A)R beta 3 subunit linked to a reporter-molecule or to a solid phase,
  (iii) the GABA(A)R having the sequence of SEQ ID NO: 1 or 2 linked to a reporter-molecule or a solid phase, or
  (iv) the cell linked to a reporter-molecule or to a solid phase and expressing the human or rat GABA(A)R alpha 1 subunit, the human or rat GABA(A)R beta 3 subunit, or the GABA(A)R having the sequence of SEQ ID NO: 1 or 2, or when the at least one liquid sample is serum, determining an antibody titer of an autoantibody to the GABA(A)R wherein the autoantibody is detectable in a serial dilution of at least 1:160 of the serum of the at least one liquid sample and detecting the presence of the binding of the autoantibody to
  (i) the human or rat GABA(A)R alpha 1 subunit linked to a reporter-molecule or to a solid phase,
  (ii) the human or rat GABA(A)R beta 3 subunit linked to a reporter-molecule or to a solid phase,
  (iii) the GABA(A)R having the sequence of SEQ ID NO: 1 or 2 linked to a reporter-molecule or to a solid phase, or
  (iv) the cell linked to a reporter-molecule or to a solid phase and expressing the human or rat GABA(A)R alpha 1 subunit, the human or rat GABA(A)R beta 3 subunit, or the GABA(A)R having the sequence of SEQ ID NO: 1 or 2, wherein said autoimmune disease is at least one disease selected from the group consisting of seizure, encephalitis and a combination thereof.

8. The method of claim 7, wherein said autoimmune disease is selected from the group consisting of (i) the combination of encephalitis and seizure and (ii) seizure.

9. The method of claim 7, wherein said human or rat GABA(A)R alpha 1 subunit linked to a reporter-molecule or to a solid phase is according to SEQ ID NO:1 and said human or rat GABA(A)R beta 3 subunit linked to a reporter-molecule or to a solid phase is according to SEQ ID NO:2.

10. A method of detecting an autoantibody to gamma-aminobutyric acid-A receptor (GABA(A)R) in a subject, the method comprising:
  obtaining a bodily fluid sample from the subject, the subject having an autoimmune disease selected from the group consisting of encephalitis, seizure and a combination thereof, and
  detecting whether the GABA(A)R autoantibody is present in said body fluid by contacting said bodily fluid with live or fixed cells in which human or rat GABA(A)R alpha 1 subunit and human or rat GABA(A)R beta 3 subunit are coexpressed, and detecting the presence of the binding between the autoantibody to the human or rat GABA(A)R alpha 1 subunit and the human or rat GABA(A)R beta 3 subunit.

* * * * *

SEQUENCE LISTING

<160> NUMBER OF SEQ ID NOS: 9

<210> SEQ ID NO 1
<211> LENGTH: 456
<212> TYPE: PRT
<213> ORGANISM: Homo sapiens

<400> SEQUENCE: 1

Met Arg Lys Ser Pro Gly Leu Ser Asp Cys Leu Trp Ala Trp Ile Leu
1               5                   10                  15

Leu Leu Ser Thr Leu Thr Gly Arg Ser Tyr Gly Gln Pro Ser Leu Gln
            20                  25                  30

Asp Glu Leu Lys Asp Asn Thr Thr Val Phe Thr Arg Ile Leu Asp Arg
        35                  40                  45

Leu Leu Asp Gly Tyr Asp Asn Arg Leu Arg Pro Gly Leu Gly Glu Arg
    50                  55                  60

Val Thr Glu Val Lys Thr Asp Ile Phe Val Thr Ser Phe Gly Pro Val
65                  70                  75                  80

Ser Asp His Asp Met Glu Tyr Thr Ile Asp Val Phe Phe Arg Gln Ser
                85                  90                  95

Trp Lys Asp Glu Arg Leu Lys Phe Lys Gly Pro Met Thr Val Leu Arg
            100                 105                 110

Leu Asn Asn Leu Met Ala Ser Lys Ile Trp Thr Pro Asp Thr Phe Phe
        115                 120                 125

His Asn Gly Lys Lys Ser Val Ala His Asn Met Thr Met Pro Asn Lys
    130                 135                 140

Leu Leu Arg Ile Thr Glu Asp Gly Thr Leu Leu Tyr Thr Met Arg Leu
145                 150                 155                 160

Thr Val Arg Ala Glu Cys Pro Met His Leu Glu Asp Phe Pro Met Asp
                165                 170                 175

Ala His Ala Cys Pro Leu Lys Phe Gly Ser Tyr Ala Tyr Thr Arg Ala
            180                 185                 190

Glu Val Val Tyr Glu Trp Thr Arg Glu Pro Ala Arg Ser Val Val Val
        195                 200                 205

Ala Glu Asp Gly Ser Arg Leu Asn Gln Tyr Asp Leu Leu Gly Gln Thr
    210                 215                 220

Val Asp Ser Gly Ile Val Gln Ser Ser Thr Gly Glu Tyr Val Val Met
225                 230                 235                 240

Thr Thr His Phe His Leu Lys Arg Lys Ile Gly Tyr Phe Val Ile Gln
                245                 250                 255

Thr Tyr Leu Pro Cys Ile Met Thr Val Ile Leu Ser Gln Val Ser Phe
            260                 265                 270

Trp Leu Asn Arg Glu Ser Val Pro Ala Arg Thr Val Phe Gly Val Thr
        275                 280                 285

Thr Val Leu Thr Met Thr Thr Leu Ser Ile Ser Ala Arg Asn Ser Leu
    290                 295                 300

Pro Lys Val Ala Tyr Ala Thr Ala Met Asp Trp Phe Ile Ala Val Cys
305                 310                 315                 320

Tyr Ala Phe Val Phe Ser Ala Leu Ile Glu Phe Ala Thr Val Asn Tyr
                325                 330                 335

Phe Thr Lys Arg Gly Tyr Ala Trp Asp Gly Lys Ser Val Val Pro Glu
            340                 345                 350

Lys Pro Lys Lys Val Lys Asp Pro Leu Ile Lys Lys Asn Asn Thr Tyr
        355                 360                 365

```
Ala Pro Thr Ala Thr Ser Tyr Thr Pro Asn Leu Ala Arg Gly Asp Pro
    370                 375                 380

Gly Leu Ala Thr Ile Ala Lys Ser Ala Thr Ile Glu Pro Lys Glu Val
385                 390                 395                 400

Lys Pro Glu Thr Lys Pro Pro Glu Pro Lys Lys Thr Phe Asn Ser Val
                405                 410                 415

Ser Lys Ile Asp Arg Leu Ser Arg Ile Ala Phe Pro Leu Leu Phe Gly
            420                 425                 430

Ile Phe Asn Leu Val Tyr Trp Ala Thr Tyr Leu Asn Arg Glu Pro Gln
        435                 440                 445

Leu Lys Ala Pro Thr Pro His Gln
    450                 455

<210> SEQ ID NO 2
<211> LENGTH: 473
<212> TYPE: PRT
<213> ORGANISM: Homo sapiens

<400> SEQUENCE: 2

Met Trp Gly Leu Ala Gly Gly Arg Leu Phe Gly Ile Phe Ser Ala Pro
1               5                   10                  15

Val Leu Val Ala Val Val Cys Cys Ala Gln Ser Val Asn Asp Pro Gly
                20                  25                  30

Asn Met Ser Phe Val Lys Glu Thr Val Asp Lys Leu Leu Lys Gly Tyr
            35                  40                  45

Asp Ile Arg Leu Arg Pro Asp Phe Gly Gly Pro Pro Val Cys Val Gly
        50                  55                  60

Met Asn Ile Asp Ile Ala Ser Ile Asp Met Val Ser Glu Val Asn Met
65                  70                  75                  80

Asp Tyr Thr Leu Thr Met Tyr Phe Gln Gln Tyr Trp Arg Asp Lys Arg
                85                  90                  95

Leu Ala Tyr Ser Gly Ile Pro Leu Asn Leu Thr Leu Asp Asn Arg Val
            100                 105                 110

Ala Asp Gln Leu Trp Val Pro Asp Thr Tyr Phe Leu Asn Asp Lys Lys
        115                 120                 125

Ser Phe Val His Gly Val Thr Val Lys Asn Arg Met Ile Arg Leu His
130                 135                 140

Pro Asp Gly Thr Val Leu Tyr Gly Leu Arg Ile Thr Thr Thr Ala Ala
145                 150                 155                 160

Cys Met Met Asp Leu Arg Arg Tyr Pro Leu Asp Glu Gln Asn Cys Thr
                165                 170                 175

Leu Glu Ile Glu Ser Tyr Gly Tyr Thr Thr Asp Asp Ile Glu Phe Tyr
            180                 185                 190

Trp Arg Gly Gly Asp Lys Ala Val Thr Gly Val Glu Arg Ile Glu Leu
        195                 200                 205

Pro Gln Phe Ser Ile Val Glu His Arg Leu Val Ser Arg Asn Val Val
    210                 215                 220

Phe Ala Thr Gly Ala Tyr Pro Arg Leu Ser Leu Ser Phe Arg Leu Lys
225                 230                 235                 240

Arg Asn Ile Gly Tyr Phe Ile Leu Gln Thr Tyr Met Pro Ser Ile Leu
                245                 250                 255

Ile Thr Ile Leu Ser Trp Val Ser Phe Trp Ile Asn Tyr Asp Ala Ser
            260                 265                 270

Ala Ala Arg Val Ala Leu Gly Ile Thr Thr Val Leu Thr Met Thr Thr
        275                 280                 285
```

```
Ile Asn Thr His Leu Arg Glu Thr Leu Pro Lys Ile Pro Tyr Val Lys
    290                 295                 300
Ala Ile Asp Met Tyr Leu Met Gly Cys Phe Val Phe Val Phe Leu Ala
305                 310                 315                 320
Leu Leu Glu Tyr Ala Phe Val Asn Tyr Ile Phe Phe Gly Arg Gly Pro
                325                 330                 335
Gln Arg Gln Lys Lys Leu Ala Glu Lys Thr Ala Lys Ala Lys Asn Asp
                340                 345                 350
Arg Ser Lys Ser Glu Ser Asn Arg Val Asp Ala His Gly Asn Ile Leu
            355                 360                 365
Leu Thr Ser Leu Glu Val His Asn Glu Met Asn Glu Val Ser Gly Gly
    370                 375                 380
Ile Gly Asp Thr Arg Asn Ser Ala Ile Ser Phe Asp Asn Ser Gly Ile
385                 390                 395                 400
Gln Tyr Arg Lys Gln Ser Met Pro Arg Glu Gly His Gly Arg Phe Leu
                405                 410                 415
Gly Asp Arg Ser Leu Pro His Lys Lys Thr His Leu Arg Arg Arg Ser
                420                 425                 430
Ser Gln Leu Lys Ile Lys Ile Pro Asp Leu Thr Asp Val Asn Ala Ile
            435                 440                 445
Asp Arg Trp Ser Arg Ile Val Phe Pro Phe Thr Phe Ser Leu Phe Asn
    450                 455                 460
Leu Val Tyr Trp Leu Tyr Tyr Val Asn
465                 470

<210> SEQ ID NO 3
<211> LENGTH: 1371
<212> TYPE: DNA
<213> ORGANISM: Homo sapiens

<400> SEQUENCE: 3
atgaggaaaa gtccaggtct gtctgactgt ctttgggcct ggatcctcct tctgagcaca      60
ctgactggaa gaagctatgg acagccgtca ttacaagatg aacttaaaga caataccact     120
gtcttcacca ggattttgga cagactccta gatggttatg acaatcgcct gagaccagga     180
ttgggagagc gtgtaaccga agtgaagact gatatcttcg tcaccagttt cggacccgtt     240
tcagaccatg atatggaata caatagat gtattttttcc gtcaaagctg aaggatgaa      300 aggttaaaat ttaaaggacc tatgacagtc ctccggttaa ataacctaat ggcaagtaaa     360
atctggactc cggacacatt tttccacaat ggaaagaagt cagtggccca acatgacc      420 atgcccaaca aactcctgcg atcacagag atggcacct tgctgtacac catgaggctg      480
acagtgagag ctgaatgtcc gatgcatttg gaggacttcc ctatggatgc catgcttgc      540 ccactaaat ttggaagtta tgcttataca agagcagaag ttgtttatga atggaccaga      600
gagccagcac gctcagtggt tgtagcagaa atgggatcac gtctaaacca gtatgacctt     660
cttggacaaa cagtagactc tggaattgtc cagtcaagta caggagaata tgttgttatg      720
accactcatt tccacttgaa gagaaagatt ggctactttg ttattcaaac atacctgcca      780
tgcataatga cagtgattct ctcacaagtc tccttctggc tcaacagaga gtctgtacca     840
gcaagaactg tctttggagt aacaactgtg ctcaccatga acacattgag catcagtgcc     900
agaaactccc tccctaaggt ggcttatgca acagctatgg attggtttat tgccgtgtgc      960
tatgcctttg tgttctcagc tctgattgag tttgccacag taaactattt cactaagaga    1020
```

```
ggttatgcat gggatggcaa aagtgtggtt ccagaaaagc caaagaaagt aaaggatcct    1080
cttattaaga aaacaacac ttacgctcca acagcaacca gctacacccc taatttggcc     1140
aggggcgacc cgggcttagc caccattgct aaaagtgcaa ccatagaacc taaagaggtc    1200
aagcccgaaa caaaccacc agaacccaag aaaaccttta acagtgtcag caaaattgac     1260
cgactgtcaa gaatagcctt cccgctgcta tttggaatct ttaacttagt ctactgggct    1320
acgtatttaa acagagagcc tcagctaaaa gcccccacac cacatcaata g             1371
```

<210> SEQ ID NO 4
<211> LENGTH: 1422
<212> TYPE: DNA
<213> ORGANISM: Homo sapiens

<400> SEQUENCE: 4

```
atgtggggcc ttgcgggagg aaggcttttc ggcatcttct cggccccggt gctggtggct    60
gtggtgtgct gcgcccagag tgtgaacgat cccgggaaca tgtcctttgt gaaggagacg    120
gtggacaagc tgttgaaagg ctacgacatt cgcctaagac ccgacttcgg ggtcccccg     180 gtctgcgtgg ggatgaacat cgacatcgcc agcatcgaca tggtttccga agtcaacatg    240
gattatacct taaccatgta ttttcaacaa tattggagag ataaaaggct cgcctattct    300
gggatccctc tcaacctcac gcttgacaat cgagtggctg accagctatg ggtgcccgac    360
acatatttct taaatgacaa aaagtcattt gtgcatggag tgacagtgaa aaaccgcatg    420
atccgtcttc accctgatgg gacagtgctg tatgggctca gaatcaccac gacagcagca    480
tgcatgatgg acctcaggag ataccccctg gacgagcaga actgcactct ggaaattgaa    540
agctatggct acaccacgga tgacattgag ttttactggc gaggcgggga caaggctgtt    600
accggagtgg aaaggattga gctcccgcag ttctccatcg tggagcaccg tctggtctcg    660
aggaatgttg tcttcgccac aggtgcctat cctcgactgt cactgagctt cggttgaag    720 aggaacattg atacttcat tcttcagact tatatgccct ctatactgat aacgattctg    780
tcgtgggtgt ccttctggat caattatgat gcatctgctg ctagagttgc cctcgggatc    840
acaactgtgc tgacaatgac aaccatcaac acccacttc gggagacctt gcccaaaatc    900
ccctatgtca aagccattga catgtacctt atgggctgct tcgtctttgt gttcctggcc    960
cttctggagt atgccttgt caactacatt ttctttggaa gaggccctca aaggcagaag   1020
aagcttgcag aaaagacagc caaggcaaag aatgaccgtt caaagagcga aagcaaccgg    1080
gtggatgctc atgaaatat tctgttgaca tcgctggaag ttcacaatga atgaatgag     1140 gtctcaggcg gcattggcga taccaggaat tcagcaatat cctttgacaa ctcaggaatc    1200
cagtacagga aacagagcat gcctcgagaa gggcatgggc gattcctggg ggacagaagc    1260
ctcccgcaca gaagaccca tctacggagg aggtcttcac agctcaaaat taaaatacct    1320
gatctaaccg atgtgaatgc catagacaga tggtccagga tcgtgtttcc attcactttt    1380
tctcttttca acttagttta ctggctgtac tatgttaact ga                      1422
```

<210> SEQ ID NO 5
<211> LENGTH: 475
<212> TYPE: PRT
<213> ORGANISM: Homo sapiens

<400> SEQUENCE: 5

```
Met Ser Ser Pro Asn Ile Trp Ser Thr Gly Ser Ser Val Tyr Ser Thr
1               5                   10                  15
```

-continued

Pro Val Phe Ser Gln Lys Met Thr Val Trp Ile Leu Leu Leu Ser
              20                  25                  30

Leu Tyr Pro Gly Phe Thr Ser Gln Lys Ser Asp Asp Tyr Glu Asp
          35                  40                  45

Tyr Ala Ser Asn Lys Thr Trp Val Leu Thr Pro Lys Val Pro Glu Gly
 50                  55                  60

Asp Val Thr Val Ile Leu Asn Asn Leu Leu Glu Gly Tyr Asp Asn Lys
65                  70                  75                  80

Leu Arg Pro Asp Ile Gly Val Lys Pro Thr Leu Ile His Thr Asp Met
                 85                  90                  95

Tyr Val Asn Ser Ile Gly Pro Val Asn Ala Ile Asn Met Glu Tyr Thr
             100                 105                 110

Ile Asp Ile Phe Phe Ala Gln Thr Trp Tyr Asp Arg Arg Leu Lys Phe
         115                 120                 125

Asn Ser Thr Ile Lys Val Leu Arg Leu Asn Ser Asn Met Val Gly Lys
     130                 135                 140

Ile Trp Ile Pro Asp Thr Phe Phe Arg Asn Ser Lys Lys Ala Asp Ala
145                 150                 155                 160

His Trp Ile Thr Thr Pro Asn Arg Met Leu Arg Ile Trp Asn Asp Gly
                 165                 170                 175

Arg Val Leu Tyr Thr Leu Arg Leu Thr Ile Asp Ala Glu Cys Gln Leu
             180                 185                 190

Gln Leu His Asn Phe Pro Met Asp Glu His Ser Cys Pro Leu Glu Phe
         195                 200                 205

Ser Ser Tyr Gly Tyr Pro Arg Glu Glu Ile Val Tyr Gln Trp Lys Arg
     210                 215                 220

Ser Ser Val Glu Val Gly Asp Thr Arg Ser Trp Arg Leu Tyr Gln Phe
225                 230                 235                 240

Ser Phe Val Gly Leu Arg Asn Thr Thr Glu Val Val Lys Thr Thr Ser
                 245                 250                 255

Gly Asp Tyr Val Val Met Ser Val Tyr Phe Asp Leu Ser Arg Arg Met
             260                 265                 270

Gly Tyr Phe Thr Ile Gln Thr Tyr Ile Pro Cys Thr Leu Ile Val Val
         275                 280                 285

Leu Ser Trp Val Ser Phe Trp Ile Asn Lys Asp Ala Val Pro Ala Arg
     290                 295                 300

Thr Ser Leu Gly Ile Thr Thr Val Leu Thr Met Thr Thr Leu Ser Thr
305                 310                 315                 320

Ile Ala Arg Lys Ser Leu Pro Lys Val Ser Tyr Val Thr Ala Met Asp
                 325                 330                 335

Leu Phe Val Ser Val Cys Phe Ile Phe Val Phe Ser Ala Leu Val Glu
             340                 345                 350

Tyr Gly Thr Leu Arg Tyr Phe Val Ser Asn Arg Lys Pro Ser Lys Asp
         355                 360                 365

Lys Asp Lys Lys Lys Lys Asn Pro Leu Leu Arg Met Phe Ser Phe Lys
     370                 375                 380

Ala Pro Thr Ile Asp Ile Arg Pro Arg Ser Ala Thr Ile Gln Met Asn
385                 390                 395                 400

Asn Ala Thr His Leu Gln Glu Arg Asp Glu Glu Tyr Gly Tyr Glu Cys
                 405                 410                 415

Leu Asp Gly Lys Asp Cys Ala Ser Phe Phe Cys Cys Phe Glu Asp Cys
             420                 425                 430

Arg Thr Gly Ala Trp Arg His Gly Arg Ile His Ile Arg Ile Ala Lys 435                 440                 445
Met Asp Ser Tyr Ala Arg Ile Phe Phe Pro Thr Ala Phe Cys Leu Phe
            450                 455                 460

Asn Leu Val Tyr Trp Val Ser Tyr Leu Tyr Leu
465                 470                 475

<210> SEQ ID NO 6
<211> LENGTH: 1428
<212> TYPE: DNA
<213> ORGANISM: Homo sapiens

<400> SEQUENCE: 6
atgagttcgc caaatatatg gagcacagga agctcagtct actcgactcc tgtattttca      60
cagaaaatga cggtgtggat tctgctcctg ctgtcgctct accctggctt cactagccag     120
aaatctgatg atgactatga agattatgct tctaacaaaa catgggtctt gactccaaaa     180
gttcctgagg gtgatgtcac tgtcatctta acaacctgc tggaaggata tgacaataaa      240
cttcggcctg atataggagt gaagccaacg ttaattcaca cagacatgta tgtgaatagc     300
attggtccag tgaacgctat caatatggaa tacactattg atatatttt tgcgcaaacg      360 tggtatgaca cacgtttgaa atttaacagc accattaaag tcctccgatt gaacagcaac     420
atggtgggga aaatctggat tccagacact ttcttcagaa attccaaaaa agctgatgca     480
cactggatca ccacccccaa caggatgctg agaatttgga tgatggtcg agtgctctac      540 accctaaggt tgacaattga tgctgagtgc caattacaat tgcacaactt tccaatggat     600
gaacactcct gccccttgga gttctcaagt tatggctatc cacgtgaaga aattgtttat     660
caatggaagc gaagttctgt tgaagtgggc gacacaagat cctggaggct ttatcaattc     720
tcatttgttg gtctaagaaa taccaccgaa gtagtgaaga caacttccgg agattatgtg     780
gtcatgtctg tctacttga tctgagcaga agaatgggat actttaccat ccagacctat     840
atcccctgca cactcattgt cgtcctatcc tgggtgtctt tctggatcaa taaggatgct     900
gttccagcca gaacatcttt aggtatcacc actgtcctga caatgaccac cctcagcacc     960
attgcccgga atcgctccc caaggtctcc tatgtcacag cgatggatct ctttgtatct    1020
gtttgtttca tctttgtctt ctctgctctg gtggagtatg gcaccttgcg ttattttgtc    1080
agcaaccgga accaagcaa ggacaaagat aaaaagaaga aaacctctc tcttcggatg     1140 tttttccttca aggccctac cattgatatc cgcccaagat cagcaaccat tcaaatgaat    1200
aatgctacac accttcaaga gagagatgaa gagtacggct atgagtgtct ggacggcaag    1260
gactgtgcca gtttttctg ctgttttgaa gattgtcgaa caggagcttg gagacatggg    1320
aggatacata tccgcattgc caaaatggac tcctatgctc ggatcttctt ccccactgcc    1380
ttctgcctgt ttaatctggt ctattgggtc tcctacctct acctgtga              1428

<210> SEQ ID NO 7
<211> LENGTH: 14
<212> TYPE: PRT
<213> ORGANISM: Rattus sp.

<400> SEQUENCE: 7

Arg Leu His Pro Asp Gly Thr Val Leu Tyr Gly Leu Arg Ile
1               5                   10

<210> SEQ ID NO 8
<211> LENGTH: 13
<212> TYPE: PRT

```
<213> ORGANISM: Rattus sp.

<400> SEQUENCE: 8

Arg Asn Val Val Phe Ala Thr Gly Ala Tyr Pro Arg Leu
1               5                   10

<210> SEQ ID NO 9
<211> LENGTH: 17
<212> TYPE: PRT
<213> ORGANISM: Rattus sp.

<400> SEQUENCE: 9

Arg Val Ala Asp Leu Trp Val Pro Asp Thr Tyr Phe Leu Asp Lys Lys
1               5                   10                  15

Ser
```